(12) United States Patent
Hinton et al.

(10) Patent No.: US 10,150,814 B2
(45) Date of Patent: Dec. 11, 2018

(54) FC VARIANTS WITH IMPROVED COMPLEMENT ACTIVATION

(71) Applicant: AbbVie Biotherapeutics Inc., Redwood City, CA (US)

(72) Inventors: Paul R. Hinton, Sunnyvale, CA (US); Veronica Juan, Redwood City, CA (US)

(73) Assignee: AbbVie Biotherapeutics Inc., Redwood City, CA (US)

( * ) Notice: Subject to any disclaimer, the term of this patent is extended or adjusted under 35 U.S.C. 154(b) by 303 days.

(21) Appl. No.: 14/901,702

(22) PCT Filed: Jun. 25, 2014

(86) PCT No.: PCT/US2014/044169
§ 371 (c)(1),
(2) Date: Dec. 28, 2015

(87) PCT Pub. No.: WO2014/210209
PCT Pub. Date: Dec. 31, 2014

(65) Prior Publication Data
US 2016/0137732 A1    May 19, 2016

Related U.S. Application Data

(60) Provisional application No. 61/840,325, filed on Jun. 27, 2013.

(51) Int. Cl.
| | | |
|---|---|---|
| *C07K 1/00* | (2006.01) | |
| *C07K 16/00* | (2006.01) | |
| *C12P 21/08* | (2006.01) | |
| *A61K 39/395* | (2006.01) | |
| *C07K 16/28* | (2006.01) | |
| *A61K 47/48* | (2006.01) | |

(52) U.S. Cl.
CPC ...... *C07K 16/283* (2013.01); *A61K 47/48561* (2013.01); *C07K 16/00* (2013.01); *C07K 16/2833* (2013.01); *C07K 2317/24* (2013.01); *C07K 2317/31* (2013.01); *C07K 2317/524* (2013.01); *C07K 2317/526* (2013.01); *C07K 2317/53* (2013.01); *C07K 2317/71* (2013.01); *C07K 2317/72* (2013.01); *C07K 2317/732* (2013.01); *C07K 2317/734* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 2004/0110226 A1* | 6/2004 | Lazar | ...... | C07K 16/00 435/7.1 |
| 2012/0258092 A1* | 10/2012 | Dahiyat | ...... | C07K 16/00 424/133.1 |

FOREIGN PATENT DOCUMENTS

| | | |
|---|---|---|
| EP | 2119780 A1 | 11/2009 |
| WO | WO 2006/076594 A2 | 7/2006 |
| WO | WO 2010/095031 A2 | 8/2010 |
| WO | WO 2011/104604 A2 | 9/2011 |

OTHER PUBLICATIONS

International Search Report and Written Opinion dated Mar. 11, 2015 corresponding to related International Patent Application No. PCT/US2014/044169.
International Preliminary Report on Patentability dated Jan. 7, 2016 corresponding to related International Patent Application No. PCT/US2014/044169.
Idusogie et al. 2001, "Engineered Antibodies with Increased Activity to Recruit Complement," *J. Immunol* 166:2571-2575.
Moore et al. 2010, "Engineered Fc variant antibodies with enhanced ability to recruit complement and mediate effector functions," *mAbs* 2(2):181-189.
Natsuma et al. 2009, "Improving effector functions of antibodies for cancer treatment: Enhancing ADCC and CDC," *Drug Des Devel Ther* 3:7-16.
Shields et al., 2001 "High Resolution Mapping of the Binding Site on Human IgG1 for FcγRI, FcγRII, and FcRn and Design of IgG1 Variants with Improved Binding to the FcγR," *J. Biological Chem* 276(9):6591-6604.
Wilson et al. 2011, "An Fcγ Receptor-Dependent Mechanism Drives Antibody-Mediated Target-Receptor Signaling in Cancer Cells," *Cancer Cell* 19(1):101-113.

* cited by examiner

*Primary Examiner* — Chun W Dahle
(74) *Attorney, Agent, or Firm* — Dechert LLP

(57) ABSTRACT

The present disclosure relates to polypeptide variants having modified Fc domains with improved potency and efficacy in activation of complement-dependent cytotoxicity.

Figure 1:
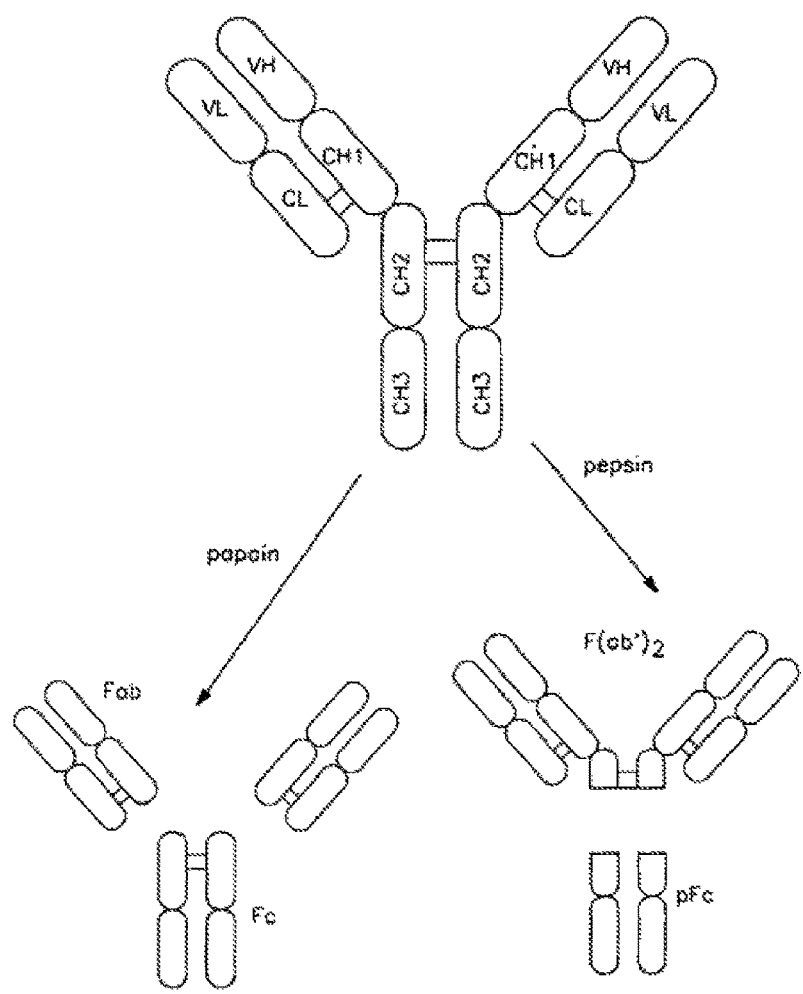

14 Claims, 13 Drawing Sheets
Specification includes a Sequence Listing.

CH1

```
118  A S T K G P S V F P L A P S S K S T S G
138  G T A A L G C L V K D Y F P E P V T V S
158  W N S G A L T S G V H T F P A V L Q S S
178  G L Y S L S S V V T V P S S S L G T Q T
198  Y I C N V N H K P S N T K V D K K V
```

Hinge

```
216  E P K S C D K T H T C P P C P
```

CH2

```
231  A P E L L G G P S V F L F P P K P K D T
251  L M I S R T P E V T C V V V D V S H E D
271  P E V K F N W Y V D G V E V H N A K T K
291  P R E E Q Y N S T Y R V V S V L T V L H
311  Q D W L N G K E Y K C K V S N K A L P A
331  P I E K T I S K A K
```

CH3

```
341  G Q P R E P Q V Y T L P P S R E E M T K
361  N Q V S L T C L V K G F Y P S D I A V E
381  W E S N G Q P E N N Y K T T P P V L D S
401  D G S F F L Y S K L T V D K S R W Q Q G
421  N V F S C S V M H E A L H N H Y T Q K S
441  L S L S P G K
```

FIG. 3

|  |  | Fold Increase | |
| --- | --- | --- | --- |
| Mutant | N | EC50 | Max. % Lysis |
| WT | 4 | 1.00 | 1.00 |
| I332G | 1 | 1.46 | 1.34 |
| S324Y | 1 | 1.91 | 0.94 |
| S324M | 1 | 2.00 | 0.89 |
| I332M | 2 | 2.47 | 1.18 |
| I332F | 1 | 2.62 | 1.23 |
| I332Y | 2 | 3.40 | 1.38 |
| N276K/A339T | 2 | 5.20 | 1.33 |
| S324W | 2 | 10.2 | 1.42 |
| S324N | 2 | 10.9 | 1.38 |
| K326M/E333S | 2 | 23.4 | 1.55 |

FIG. 7

|  |  | Fold Increase | |
| --- | --- | --- | --- |
| Mutant | N | EC50 | Max. % Lysis |
| A330L | 3 | 0.39 | 0.63 |
| WT | 3 | 1.00 | 1.00 |
| H268F/S324T | 3 | 7.21 | 1.29 |
| N276K/A339T | 3 | 7.29 | 1.24 |
| S324N/I332F | 3 | 12.8 | 1.37 |
| K326M/E333S | 3 | 13.1 | 1.33 |
| S267E/H268F/S324T | 3 | 13.5 | 1.44 |
| S324N/I332M | 3 | 13.6 | 1.39 |
| S324W/I332F | 3 | 13.7 | 1.41 |
| S324W/I332M | 3 | 15.5 | 1.37 |
| S324N/I332Y | 3 | 20.1 | 1.35 |
| S324W/I332Y | 3 | 23.1 | 1.38 |

FIG. 8

|    | S324 Substitution | I332 Substitution |
|----|-------------------|-------------------|
| 1  | S324M             |                   |
| 2  | S324M             | I332F             |
| 3  | S324M             | I332G             |
| 4  | S324M             | I332M             |
| 5  | S324M             | I332Y             |
| 6  | S324N             |                   |
| 7  | S324N             | I332F             |
| 8  | S324N             | I332G             |
| 9  | S324N             | I332M             |
| 10 | S324N             | I332Y             |
| 11 | S324W             |                   |
| 12 | S324W             | I332F             |
| 13 | S324W             | I332G             |
| 14 | S324W             | I332M             |
| 15 | S324W             | I332Y             |
| 16 | S324Y             |                   |
| 17 | S324Y             | I332F             |
| 18 | S324Y             | I332G             |
| 19 | S324Y             | I332M             |
| 20 | S324Y             | I332Y             |
| 21 |                   | I332F             |
| 22 |                   | I332G             |
| 23 |                   | I332M             |
| 24 |                   | I332Y             |

FIG. 9

| Sequence ID | Description | Sequence |
|---|---|---|
| 1 | WT | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 2 | WT CH2 | APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK |
| 3 | WT CH3 G1m (z, non a) allotype | GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 4 | WT CH3 G1m (z, a) allotype | GQPREPQVYT LPPSRDELTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 5 | 324M | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVMNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 6 | 324N | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVNNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

FIG. 10A

| Sequence ID | Description | Sequence |
|---|---|---|
| 7 | 324W | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVWNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 8 | 324Y | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVYNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 9 | 332F | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPFEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 10 | 332G | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPGEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

FIG. 10B

| Sequence ID | Description | Sequence |
|---|---|---|
| 11 | 332M | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPMEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 12 | 332Y | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPYEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 13 | 324N/332F | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVNNKA LPAPFEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 14 | 324W/332F | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVWNKA LPAPFEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

FIG. 10C

| Sequence ID | Description | Sequence |
|---|---|---|
| 15 | 324N/332M | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVNNKA LPAPMEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 16 | 324W/332M | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVWNKA LPAPMEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 17 | 324N/332Y | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVNNKA LPAPYEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 18 | 324W/332Y | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVWNKA LPAPYEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

FIG. 10D

SEQUENCE LISTING

```
<160> NUMBER OF SEQ ID NOS: 38

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
            65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 110
<212> TYPE: PRT
<213> ORGANISM: Homo sapiens

<400> SEQUENCE: 2

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 3
<211> LENGTH: 107
<212> TYPE: PRT
<213> ORGANISM: Homo sapiens

<400> SEQUENCE: 3

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 4
<211> LENGTH: 107
<212> TYPE: PRT
<213> ORGANISM: Homo sapiens

<400> SEQUENCE: 4

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 5
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                  85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Met Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 6
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Asn Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Trp Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 8
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Tyr Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys

```
            130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Phe Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 10
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Gly Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 11
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Met Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
```

```
            195                 200                 205
Lys Ala Leu Pro Ala Pro Tyr Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 13
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Asn Asn
        195                 200                 205

Lys Ala Leu Pro Ala Pro Phe Glu Lys Thr Ile Ser Lys Ala Lys Gly
    210                 215                 220
```

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 14
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Trp Asn
        195                 200                 205

Lys Ala Leu Pro Ala Pro Phe Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 15
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Asn Asn
        195                 200                 205

Lys Ala Leu Pro Ala Pro Met Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
```

```
                    260                 265                 270
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 16
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Trp Asn
        195                 200                 205

Lys Ala Leu Pro Ala Pro Met Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Asn Asn
        195                 200                 205

Lys Ala Leu Pro Ala Pro Tyr Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

```
Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 18
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Trp Asn
        195                 200                 205

Lys Ala Leu Pro Ala Pro Tyr Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

-continued

```
                325                 330
```

<210> SEQ ID NO 19
<211> LENGTH: 98
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 20
<211> LENGTH: 15
<212> TYPE: PRT
<213> ORGANISM: Homo sapiens

<400> SEQUENCE: 20

Glu Pro Lys Ser Cys Asp Lys Thr His Thr Cys Pro Pro Cys Pro
1               5                   10                  15

<210> SEQ ID NO 21
<211> LENGTH: 110
<212> TYPE: PRT
<213> ORGANISM: Homo sapiens

<400> SEQUENCE: 21

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 22
<211> LENGTH: 5
<212> TYPE: PRT
<213> ORGANISM: Mus sp.

<400> SEQUENCE: 22

Ala Asp Ala Ala Pro

```
1               5

<210> SEQ ID NO 23
<211> LENGTH: 5
<212> TYPE: PRT
<213> ORGANISM: Homo sapiens

<400> SEQUENCE: 23

Thr Val Ala Ala Pro
1               5

<210> SEQ ID NO 24
<211> LENGTH: 11
<212> TYPE: PRT
<213> ORGANISM: Mus sp.

<400> SEQUENCE: 24

Ala Asp Ala Ala Pro Thr Val Ser Ile Phe Pro
1               5                   10

<210> SEQ ID NO 25
<211> LENGTH: 12
<212> TYPE: PRT
<213> ORGANISM: Homo sapiens

<400> SEQUENCE: 25

Thr Val Ala Ala Pro Ser Val Phe Ile Phe Pro Pro
1               5                   10

<210> SEQ ID NO 26
<211> LENGTH: 6
<212> TYPE: PRT
<213> ORGANISM: Homo sapiens

<400> SEQUENCE: 26

Gln Pro Lys Ala Ala Pro
1               5

<210> SEQ ID NO 27
<211> LENGTH: 13
<212> TYPE: PRT
<213> ORGANISM: Homo sapiens

<400> SEQUENCE: 27

Gln Pro Lys Ala Ala Pro Ser Val Thr Leu Phe Pro Pro
1               5                   10

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Gly Ser Gly Gly
1               5

<210> SEQ ID NO 29
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 29

Gly Gly Ser Gly Gly Gly Gly Ser Gly
1               5

<210> SEQ ID NO 30
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Gly Ser Gly Gly Gly Gly Ser Gly Gly Gly Gly Ser
1               5                   10

<210> SEQ ID NO 31
<211> LENGTH: 6
<212> TYPE: PRT
<213> ORGANISM: Mus sp.

<400> SEQUENCE: 31

Ala Lys Thr Thr Ala Pro
1               5

<210> SEQ ID NO 32
<211> LENGTH: 6
<212> TYPE: PRT
<213> ORGANISM: Homo sapiens

<400> SEQUENCE: 32

Ala Ser Thr Lys Gly Pro
1               5

<210> SEQ ID NO 33
<211> LENGTH: 13
<212> TYPE: PRT
<213> ORGANISM: Mus sp.

<400> SEQUENCE: 33

Ala Lys Thr Thr Ala Pro Ser Val Tyr Pro Leu Ala Pro
1               5                   10

<210> SEQ ID NO 34
<211> LENGTH: 13
<212> TYPE: PRT
<213> ORGANISM: Homo sapiens

<400> SEQUENCE: 34

Ala Ser Thr Lys Gly Pro Ser Val Phe Pro Leu Ala Pro
1               5                   10

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35
```

```
-continued

Gly Gly Gly Gly Ser Gly
1               5

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gly Gly Gly Gly Ser Gly Gly Gly Gly Ser
1               5                   10

<210> SEQ ID NO 37
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Gly Gly Gly Ser Gly Gly Gly Gly Ser Gly Gly Gly Gly
1               5                   10

<210> SEQ ID NO 38
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 38

His His His His His His
1               5
```

FC VARIANTS WITH IMPROVED COMPLEMENT ACTIVATION

This application is a National Stage Entry of International Application No. PCT/US2014/44169, filed Jun. 25, 2014, which claims priority under 35 U.S.C. § 119(e) to provisional application Ser. No. 61/840,325, filed Jun. 27, 2013, the contents of all of which are incorporated by reference herein in their entireties by reference thereto.

The instant application contains a Sequence Listing, which has been submitted electronically in ASCII format via EFS-Web and is hereby incorporated by reference in its entirety. Said ASCII copy, created on Dec. 28, 2015, is named 918WO_Seq_Listing.txt and is 53,100 bytes in size.

1. BACKGROUND

The main mechanisms of action for therapeutic IgG antibodies are direct effects (e.g., apoptosis), ADCC (antibody-dependent cell-mediated cytotoxicity) and CDC (complement-dependent cytotoxicity). The human IgG1 isotype in particular can induce strong ADCC and CDC when compared with the other heavy chain isotypes. CDC effector functions are activated through the interactions of the fragment crystallizable ("Fc") regions of IgG molecules with complement. An Fc region of an immunoglobulin is composed of two identical protein fragments, derived from the second and third constant domains of the antibody's two heavy chains (depicted in FIG. 1).

CDC is a cytolytic cascade mediated by a series of complement proteins present in serum. It is triggered by the binding of complement protein C1q to the Fc region of an antibody molecule (Natsume et al., 2009, Drug Des. Devel. Ther. 3:7-16). The signaling pathway of the complement system, shown in FIG. 2, triggers targeted cellular destruction via the membrane-attack complex (MAC), a transmembrane channel formed by association of complement proteins. Loss of membrane integrity via the MAC results in cell swelling and lysis.

Antibodies with enhanced CDC are thought to be more effective as therapeutics. Arzerra (ofatumumab) is an anti-CD20 antibody used in the treatment of chronic lymphocytic leukemia (CLL). Ofatumumab was selected on the basis of its higher CDC activity compared to an earlier anti-CD20 antibody, Rituxan (Pawluczkowycz et al., 2009, J. Immunol. 183:749-758). CDC is also thought to be an important mechanism of action of the anti-CD52 antibody alemtuzumab (Campath-1H) (Natsume et al., 2009, Drug Des. Devel. Ther. 3:7-16).

The binding of the C1q component to the Fc, the initial step of the complement cascade, affects the intensity of the following complement activation, and several approaches have succeeded in enhancing CDC by facilitating the binding of the antibody constant region to C1q. As a result of engineered amino acid mutations inserted into either Fc or the hinge region, designed antibody constant regions possessing improved C1q binding have been achieved (Natsume et al., 2009, Drug Des. Devel. Ther. 3:7-16).

Nonetheless, there remains a need for identification of further amino acid substitutions in Fc molecules that modulate the interaction between Fc and C1q in order to enhance CDC activation and therefore efficacy of Fc-containing therapeutic molecules, particularly for indications such as cancer where cell death of the target cell is desired.

2. SUMMARY

The present disclosure relates to modifying the biological activity, including complement-dependent cytotoxicity (CDC), of molecules containing Fc moieties, by modulating the binding of Fc moieties to the C1q protein. The present disclosure accordingly provides polypeptides comprising variant Fc domains with altered affinities to C1q. In some embodiments, where cell lysis through the complement cascade is desired (e.g., for cancer indications), the Fc domains have greater affinity to C1q than a wild type Fc domain.

The Fc moiety can be an IgG Fc domain, for example an IgG1 or IgG3 Fc domain. The Fc domain includes a CH2 domain or a CH3 domain, preferably both. In some embodiments, the Fc domain includes a hinge region, a CH2 domain and a CH3 domain. The Fc and C1q sequences are preferably both from the same species, most preferably human. An exemplary Fc sequence is that of human IgG1, provided as SEQ ID NO:1.

Accordingly, in one aspect, the present disclosure provides polypeptides comprising modified (or variant) CH2 domains or entire Fc domains (collectively referred to as "variant polypeptides" or "variant Fc polypeptides") that include amino acid substitutions that increase binding to C1q as compared to the binding of a corresponding wild-type CH2 or Fc region. A polypeptide of the disclosure can be a monomer or multimer (e.g., dimer or tetramer), each monomeric unit comprising one or more CH2 or Fc domains of the disclosure. A polypeptide of the disclosure is typically an antibody or an Fc fusion protein comprising a variant CH2 or Fc domain of the disclosure. A variant CH2 or variant Fc domain of the present disclosure typically includes one or more substitutions identified or pairs of substitutions identified in FIG. 9.

A variant CH2 or variant Fc domain of the present disclosure can have increased, decreased or unaltered ADCC activity as compared to a corresponding wild-type CH2 or Fc domain.

Thus, in one aspect, the present disclosure provides polypeptides comprising a variant CH2 domain which has at least 70%, at least 75%, at least 80%, at least 85%, at least 90%, at least 95%, at least 96%, at least 97%, at least 98% or at least 99% sequence identity to the CH2 domain of SEQ ID NO:2.

In another aspect, the present disclosure provides polypeptides comprising a variant CH2 which has up to 6, up to 5, up to 4, up to 3, up to 2 substitutions, or a single amino acid substitution as compared to an CH2 domain of SEQ ID NO:2, including at least one amino acid substitution at position 324 and/or at least one amino acid substitution at position 332. Exemplary individual or double substitutions that can be incorporated into the polypeptide of the disclosure are identified in FIG. 9.

As discussed in detail herein, the variant CH2 domain is a component of the Fc domain of an antibody. Accordingly, in one aspect polypeptides are provided that comprise an Fc domain, said Fc domain comprising a variant CH2 domain of the disclosure. In some embodiments, the Fc domain has up to 20, up to 15, up to 12, up to 10, up to 9, up to 8, up to 7, up to 6, up to 5 or up to 4 amino acid substitutions as compared to the CH2 of SEQ ID NO:2, or as compared to the Fc domain of SEQ ID NO:1. Overall, the Fc domain of the polypeptide can have at least 70%, at least 75%, at least 80%, at least 85%, at least 90%, at least 95%, at least 96%, at least 97%, at least 98% or at least 99% sequence identity to the Fc domain of SEQ ID NO:1.

Skilled artisans will appreciate that disclosed Fc domains can comprise any of the one or more CH2 substitutions described herein. The variant Fc domains can further include additional substitutions, such as known substitutions that modify effector function, such as C1q binding or substitutions that modify CDC activity.

Fc domains are known to mediate Fc effector functions, as described in Section 4.5. The disclosure provides polypeptides that further comprise one or more additional substitutions or combinations of substitutions that modify Fc effector function. Typically, Fc effector functions that can be modified include (a) reduction or increase in binding to FcRn; (b) reduction or increase in binding to FcγRI; (c) reduction or increase in binding to FcγRIIA or FcγRIIB; (d) reduction or increase in binding to FcγRIIIA; (e) reduction or increase in binding to C1q; or (f) a combination of two, three, four or all of the foregoing.

In one aspect, the disclosure provides polypeptides that are antibodies, discussed in further detail in Section 4.1. These antibodies can be human or humanized antibodies. In typical embodiments, an antibody specifically binds to a costimulatory molecule, a cytokine, a chemokine, an adhesion molecule, an activation marker, or an immunomodulatory protein. Polypeptides of the disclosure also include Fc fusion proteins in which the variant CH2 domain is part of an Fc domain operably linked to at least one fusion partner. Fc fusion proteins are discussed in detail in Section 4.3.

In another aspect, the disclosure provides conjugate compounds comprising polypeptides the disclosure linked to an effector moiety or a detectable label. Conjugate compounds are discussed further in Section 4.6. In some embodiments, the conjugate compound comprises a polypeptide linked to a detectable label, such as a radioactive compound, a fluorescent compound, an enzyme, a substrate, an epitope tag or a toxin. In some embodiments, the conjugate compound comprises a polypeptide linked to an effector moiety, such as a cytotoxic agent or anti-tubulin. Skilled artisans will appreciate the various cytotoxic agents that can be linked to polypeptides of the disclosure, including an auristatin (e.g., monomethyl auristatin E (MMAE) or monomethyl auristatin F (MMAF)), a DNA minor groove binding agent, a DNA minor groove alkylating agent, an enediyne, a duocarmycin, a maytansinoid (e.g., DM1 or DM4) or a vinca alkaloid.

The present disclosure further provides pharmaceutical compositions comprising polypeptides of the disclosure and a pharmaceutically acceptable carrier or a conjugate compound of the disclosure. Pharmaceutical compositions and methods of treatment are discussed in detail in Section 4.7.

Nucleic acids comprising nucleotide sequences encoding the polypeptides of the disclosure are provided herein, as are vectors comprising nucleic acids. Additionally, prokaryotic and eukaryotic host cells transformed with a vector comprising a nucleotide sequence encoding a disclosed polypeptide are provided herein, as well as eukaryotic (such as mammalian) host cells engineered to express the nucleotide sequences. Methods of producing polypeptides, by culturing host cells and recovering the polypeptides are also provided, and discussed further in Section 4.4, below.

Skilled artisans will appreciate that the polypeptides of the disclosure are useful in the treatment of various diseases or disorders such as an immune disorder or cancer for which it would be suitable to administer to a patient in need thereof an appropriate polypeptide, pharmaceutical composition, or conjugate compound of the disclosure.

It should be understood that the above summary is not intended to describe every embodiment or every implementation of the various inventions disclosed herein. The Detailed Description and Examples Section further exemplify illustrative embodiments. The various embodiments described herein are intended to be disclosed in combinations, as if each specific combination were explicitly disclosed. The Examples are representative only and should not be interpreted as exclusive, or limiting the scope of the various inventions disclosed herein.

A more complete appreciation of the various inventions disclosed herein, and many of the attendant advantages thereof, is provided by the detailed description that follows.

As used herein throughout the specification and in the appended claims, the following terms and expressions are intended to have the following meanings:

The indefinite articles "a" and "an" and the definite article "the" are intended to include both the singular and the plural, unless the context in which they are used clearly indicates otherwise.

"At least one" and "one or more" are used interchangeably to mean that the article may include one or more than one of the listed elements.

Unless otherwise indicated, it is to be understood that all numbers expressing quantities, ratios, and numerical properties of ingredients, reaction conditions, and so forth, used in the specification and claims are contemplated to be able to be modified in all instances by the term "about."

3. BRIEF DESCRIPTION OF THE FIGURES

FIG. 1 provides a schematic representation of a native IgG. Disulfide bonds are represented by heavy lines between CH1 and CL domains and the two CH2 domains. V is variable domain; C is constant domain; L stands for light chain and H stands for heavy chain.

Figure 2:
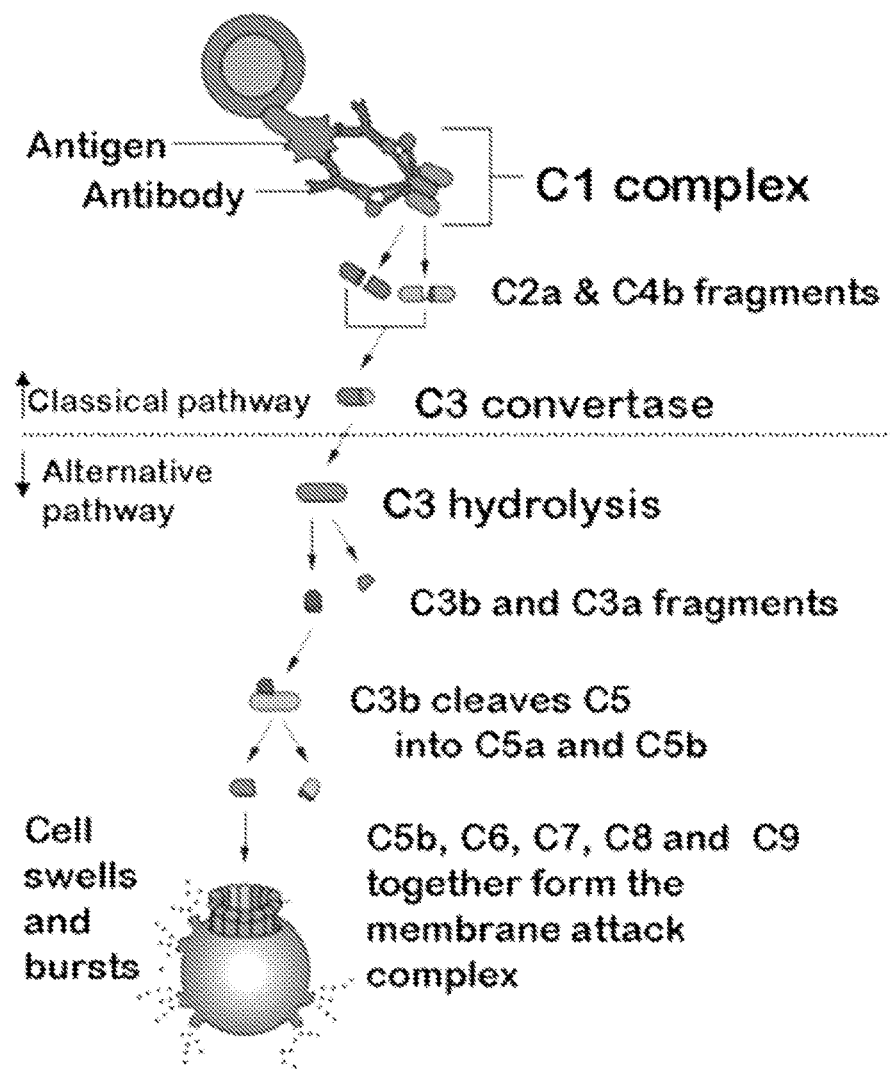

FIG. 2 provides a schematic representation of activation of the antibody-dependent classical complement-dependent cytotoxicity pathway.

FIG. 3 shows the amino acid sequences and the numbering of the amino acids in the CH1, hinge, CH2 and CH3 domains. The Fc sequence shown is that of the human G1m (z, non a) allotype, whose CH3 domain is GQPREPQVYTLPPSREEMTKNQVSLTCLVKGFYPS-DIAVEWESNGQPENNYKTTPPVLDS DGSFFLYSKLT-VDKSRWQQGNVFSCSVMHEALHNHYTQK-SLSLSPGK; SEQ ID NO:3. The human G1m (z, a) allotype can also be used, which differs in its CH3 sequence. The sequence of the CH3 domain in the G1m (z, a) allotype is GQPREPQVYTLPPSRDELTKNQVSLTCLVKGFYPS-DIAVEWESNGQPENNYKTTPPVLDS DGSFFLYSKLT-VDKSRWQQGNVFSCSVMHEALHNHYTQK-SLSLSPGK; SEQ ID NO:4.

FIGS. 4A-4D show complement-dependent cytotoxicity of single-mutant variants of the disclosure.

Figure 5:
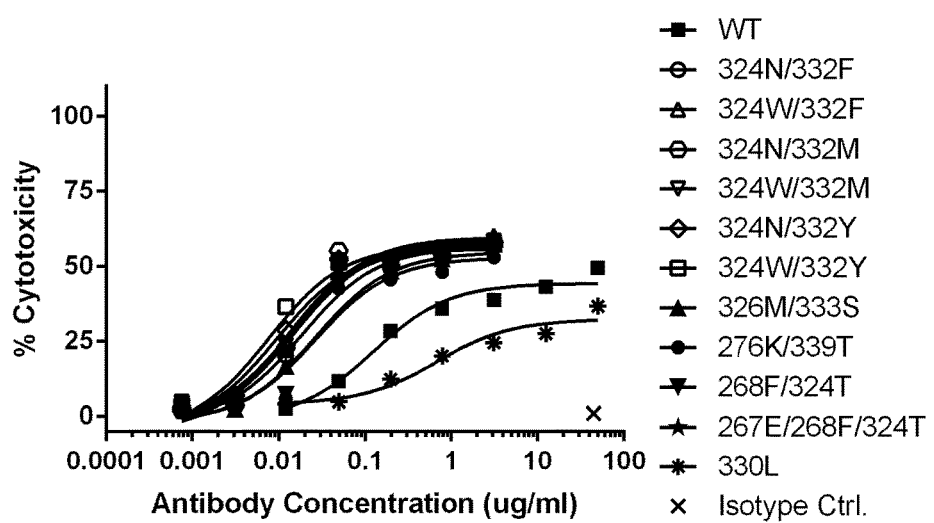

FIG. 5 provides complement-dependent cytotoxicity of double-mutant variants of the disclosure.

Figure 6A:
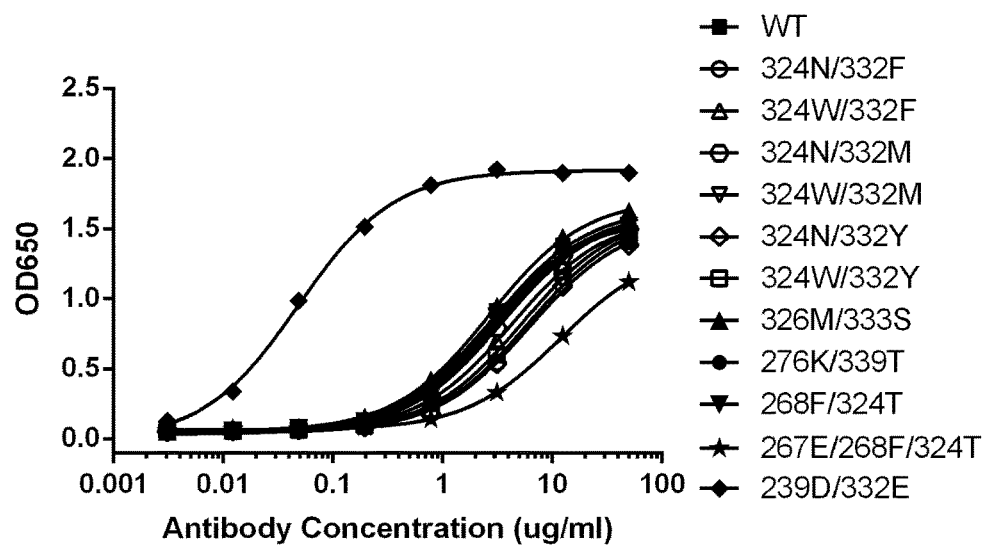
Figure 6B:
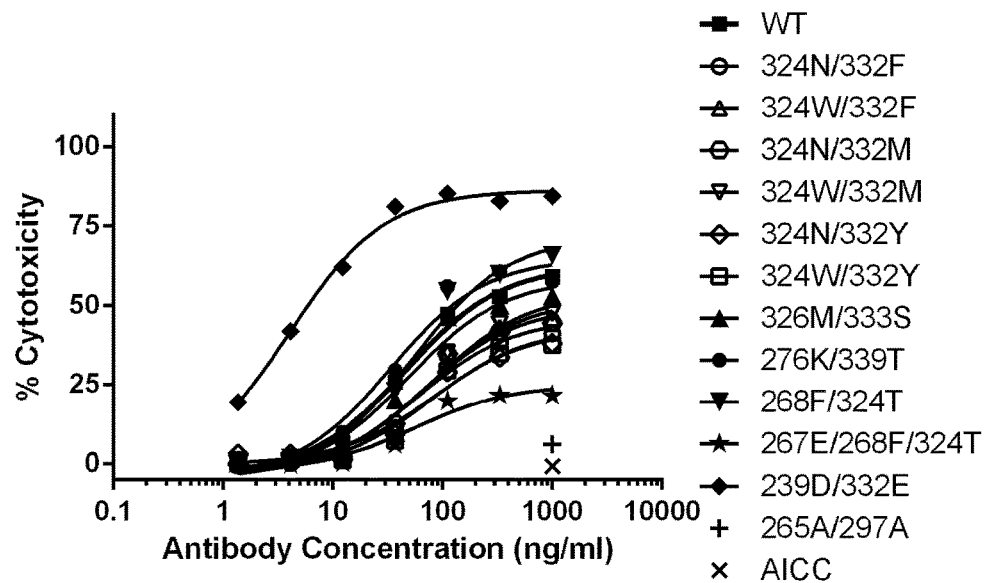

FIGS. 6A-6B provide FcγRIIIA binding and ADCC activity of variants of the disclosure, respectively.

FIG. 7 provides a summary of Fc single substitutions that can be incorporated into the polypeptides of the disclosure to modify effector function.

FIG. 8 provides a summary of Fc double substitutions that can be incorporated into the polypeptides of the disclosure to modify effector function.

FIG. 9 provides exemplary single and double amino acid substitutions that can be incorporated into the variants of the disclosure.

FIGS. 10A-10D provide sequence listing.

4. DETAILED DESCRIPTION 4.1. Fc Variant Polypeptides

Fc domains of immunoglobulin are involved in non-antigen binding function and have several effector functions mediated by binding of effector molecules. As illustrated in FIG. 1, Fc domains are composed of two main domains, the CH2 domain and the CH3 domain, and have a small hinge region N-terminal to the CH2 domain. The present disclosure provides polypeptides comprising modified CH2 domains (and modified Fc domains comprising modified CH2 domains), collectively referred to herein as variant polypeptides, Fc variants, or simply variants or polypeptides. The variant polypeptides are typically antibodies or antibody fragments (referred to herein collectively as antibody variants) or Fc fusion proteins.

As used herein, numbering of antibody amino acid residues is done according to Kabat EU nomenclature unless otherwise indicated.

As used herein, the term "Fc domain" refers to a C-terminal region of an immunoglobulin heavy chain. Although the generally accepted boundaries of the Fc domain of an immunoglobulin heavy chain might vary, the human IgG heavy chain Fc domain is usually defined to stretch from an amino acid residue at position Cys226, or from Pro230, to the carboxyl-terminus thereof. In some embodiments, variants comprise only portions of the Fc domain and can include or not include the carboxyl-terminus. The Fc domain of an immunoglobulin generally comprises two constant domains, CH2 and CH3. The Fc variant polypeptides of the disclosure typically include at a CH2 domain and oftentimes also include a CH3 domain.

As used herein, the "CH2 domain" (also referred to as "Cγ2" domain) generally comprises the stretch of residues that extends from about amino acid 231 to about amino acid 340 in an Fc domain (e.g., in the human IgG Fc domain). The CH2 domain is unique in that it is not closely paired with another domain. Rather, two N-linked branched carbohydrate chains are interposed between the two CH2 domains of an intact native IgG molecule.

As used herein, the "CH3 domain" (also referred to as "Cγ3" domain) generally comprises the stretch of residues C-terminal to a CH2 domain in an Fc domain (e.g., from about amino acid residue 341 to about amino acid residue 447 of a human IgG Fc region).

The polypeptides of the disclosure comprise an Fc variant domain having an amino acid sequence substantially homologous to all or part of a human immunoglobulin constant region ("C region"), preferably an IgG constant domain C region.

Numerous sequences for human C regions have been published; see, e.g., Clark, 1997, Chem. Immunol. 65:88-110. Other sequences for human immunoglobulin heavy chains can be obtained from the SwissProt and PIR databases using Lasergene software (DNAStar Limited, London UK) under accession numbers A93433, B90563, A90564, B91668, A91723 and A02146 for human Igγ-1 chain C region, A93906, A92809, A90752, A93132, A02148 for human Igγ-2 chain C region, A90933, A90249, A02150 for human Igγ-4 chain C region, and A23511 for human Igγ-3 chain C region. An exemplary Fc domain has the amino acid sequence of SEQ ID NO:1.

In various embodiments, the amino acid sequence of the Fc variant domain shares at least about 70%, 75%, 80%, 85%, 90%, 95%, 96%, 97%, 98% or 99% sequence identity with the reference any of the foregoing Fc domains. In a preferred embodiment, the reference Fc domain comprises SEQ ID NO:1.

Sequence comparisons are typically performed by comparing sequences over a "comparison window" to identify and compare local regions of sequence similarity. A "comparison window" refers to a conceptual segment of typically 12 contiguous residues that is compared to a reference sequence. The comparison window may comprise additions or deletions (i.e., gaps) of about 20% or less as compared to the reference sequence (which does not comprise additions or deletions) for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive, Madison, Wis., incorporated herein by reference) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25:3389-402, which is incorporated herein by reference.

The present disclosure provides polypeptides comprising a modified Fc domain wherein the binding of the polypeptide to C1q is altered compared to that of the wild-type Fc domain. The polypeptide can be an antibody or an Fc fusion protein. In some embodiments, binding of the Fc is increased by virtue of the modification(s).

The Fc variant polypeptides can comprise a variant CH2 domain having at least one substitution at position S324 and/or at least one substitution at position I332, where the numbering of the residues in the Fc domain is that of the EU index as in Kabat. Exemplary single and double amino acid substitutions can that can be incorporated into the CH2 domain are set forth in FIG. 9. In addition to the substitutions set forth in FIG. 9, the variant CH2 and Fc domains of the disclosure can have one or more additional amino acid substitutions, for example one or more substitutions that modulate effector function. In certain aspects, the effector function is binding to an Fc receptor (or "FcR"), a receptor that binds to an Fc domain (e.g. the Fc domain of an antibody or antibody fragment). Examples of FcRs to which binding can be modulated by substitutions to the Fc domain include the neonatal Fc receptor, FcRn, and receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine based activation motif (ITAM) in its cytoplasmic domain Inhibiting receptor FcγRIIB contains an immunoreceptor tyrosine-based inhibition motif (ITIM) in its cytoplasmic domain. Other FcRs are encompassed by the term "FcR" herein.

Accordingly, the Fc variant polypeptides can further include substitutions that increase binding to FcRn, or reduce binding to FcRn, in order to generate variants having the optimal properties for any given therapeutic application. Such variants can incorporate substitutions at amino acid positions involved in FcRn interactions (see, e.g., WO 2005/123780), for example positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc domain, wherein the numbering of the residues in the Fc domain is that of the EU index as in Kabat. Such variant Fc domains with reduced binding to an FcRn can comprise an amino acid modification at any one or more of amino acid positions 252, 253, 254, 255, 288, 309, 386, 388, 400, 415, 433, 435, 436, 439 or 447 of the Fc domain, wherein the numbering of the residues in the Fc domain is that of the EU index as in Kabat. The above-mentioned variant Fc domains may, alternatively, contains one or more substitutions that result in increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc domain, wherein the numbering of the residues in the Fc domain is that of the EU index as in Kabat. In yet further embodiments, the variant Fc domains have at least one or more modifications that enhance the affinity to FcRn, e.g., a modification of one or more amino acid residues 251-256, 285-290, 308-314, 385-389, and 428-436 (e.g., M428L), or a modification at positions 250 and 428 (e.g., T250Q/ M428L), see, e.g., Hinton et al., 2004, J. Biol. Chem. 279:6213-6; PCT Publication No. WO 97/34631; and WO 02/060919, all of which are incorporated herein by reference in their entirety. In particular embodiments, an antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine.

In one embodiment, the variant Fc domain contains one or more substitutions that result in reduced binding to an FcγR and comprises an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc domain, wherein the numbering of the residues in the Fc domain is that of the EU index as in Kabat.

For example, the variant Fc domain can contain one or more substitutions that result in reduced binding to an FcγRI and comprise an amino acid modification at any one or more of amino acid positions 238, 265, 269, 270, 327 or 329 of the Fc domain, wherein the numbering of the residues in the Fc domain is that of the EU index as in Kabat.

The variant Fc domain can contain one or more substitutions that result in reduced binding to an FcγRII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc domain, wherein the numbering of the residues in the Fc domain is that of the EU index as in Kabat.

The variant Fc domain can contain one or more substitutions that result in reduced binding to an FcγRIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc domain, wherein the numbering of the residues in the Fc domain is that of the EU index as in Kabat.

In another embodiment, the variant Fc domain with altered FcγR binding affinity contains one or more substitutions that result in improved binding to the FcγR and comprises an amino acid modification at any one or more of amino acid positions 255, 256, 258, 267, 268, 272, 276, 280, 283, 285, 286, 290, 298, 301, 305, 307, 309, 312, 315, 320, 322, 326, 330, 331, 333, 334, 337, 340, 360, 378, 398 or 430 of the Fc domain, wherein the numbering of the residues in the Fc domain is that of the EU index as in Kabat.

For example, the variant Fc domain can contain one or more substitutions that result in increased binding to an FcγRIII and, optionally, may further contains one or more substitutions that result in decreased binding to an FcγRII. An exemplary such variant comprises amino acid modification(s) at position(s) 298 and/or 333 of the Fc domain, wherein the numbering of the residues in the Fc domain is that of the EU index as in Kabat.

The variant Fc domain can contain one or more substitutions that result in increased binding to an FcγRII and comprise an amino acid modification at any one or more of amino acid positions 255, 256, 258, 267, 268, 272, 276, 280, 283, 285, 286, 290, 301, 305, 307, 309, 312, 315, 320, 322, 326, 330, 331, 337, 340, 378, 398 or 430 of the Fc domain, wherein the numbering of the residues in the Fc domain is that of the EU index as in Kabat. Such variant Fc domains with increased binding to an FcγRII may optionally further contain one or more substitutions that result in decreased binding to an FcγRIII and may, for example, comprise an amino acid modification at any one or more of amino acid positions 268, 272, 298, 301, 322 or 340 of the Fc domain, wherein the numbering of the residues in the Fc domain is that of the EU index as in Kabat.

Other exemplary substitutions leading to modification in Fc effector function are those disclosed in U.S. Pat. No. 7,632,497, hereby incorporated by reference in its entirety.

In certain embodiments, the variant Fc regions of the disclosure include a hinge region that has one or more substitutions relative to the hinge region shown in FIG. 3 that impact effector function, for example as described in WO2009/006520, particularly at the amino acid position set forth in claim 7 of WO2009/006520. In specific embodiment, the hinge region can include at least one of the combinations of substitutions designated (a) through (ff) as set forth in claim 8 of WO2009/006520. WO2009/006520 is incorporated by reference herein in its entirety.

The variant polypeptides of the disclosure can be antibodies or Fc fusion proteins. For example but not by way of limitation, an Fc fusion protein can be an antibody that is recombinantly expressed as a fusion protein, e.g., with a cytokine protein, a toxin protein or other bioactive protein. In other embodiments, an Fc fusion protein contains an Fc domain of an antibody, such as a variant Fc domain as disclosed herein, recombinantly expressed as a fusion protein with a fusion partner. In other embodiments, an Fc fusion protein contains a CH2 domain of an Fc region, such as a variant CH2 domain as disclosed herein, recombinantly expressed as a fusion protein with a fusion partner. The variant antibodies of the disclosure can be antibody-drug conjugates. For example but not by way of limitation the variant antibodies can be conjugated to toxins or bioactive small molecule compounds. Exemplary antibodies and fusion proteins are described in Sections 4.2 and 4.3, respectively.

4.2. Variant Antibodies

The polypeptides of the disclosure can be antibodies comprising the variant Fc sequences described herein, referred to as "variant antibodies".

In certain embodiments, the variant antibodies of the disclosure are monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone and not the method by which it is produced. Monoclonal antibodies useful in connection with the present disclosure can be prepared using a wide variety of techniques known in the art including the use of hybridoma, recombinant, and phage display technologies or a combination thereof. The Fc variants of the disclosure include chimeric, primatized, humanized, or human antibodies.

The variant antibodies of the disclosure can be chimeric antibodies. The term "chimeric" antibody as used herein refers to an antibody having variable sequences derived from a non-human immunoglobulin, such as rat or mouse antibody, and human immunoglobulin constant regions, typically chosen from a human immunoglobulin template. Methods for producing chimeric antibodies are known in the art. See, e.g., Morrison, 1985, Science 229:1202-7; Oi et al., 1986, BioTechniques 4:214-221; Gillies et al., 1985, J. Immunol. Methods 125:191-202; U.S. Pat. Nos. 5,807,715; 4,816,567; and 4,816397, which are incorporated herein by reference in their entireties.

The variant antibodies of the disclosure can be humanized. "Humanized" forms of non-human (e.g., murine) antibodies are chimeric immunoglobulins, immunoglobulin chains or fragments thereof (such as Fv, Fab, Fab', F(ab')$_2$ or other target-binding subdomains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585, 089; 5,693,761; 5,693,762; and 6,180,370 to Queen et al.; EP239400; PCT publication WO 91/09967; U.S. Pat. No. 5,225,539; EP592106; EP519596; Padlan, 1991, Mol. Immunol. 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

The variant antibodies of the disclosure can be human antibodies. Completely "human" Fc variants can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625, 126; 5,633,425; 5,569,825; 5,661,016; 5,545,806; 5,814, 318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, Biotechnology 12:899-903).

The variant antibodies of the disclosure can be primatized. The term "primatized antibody" refers to an antibody comprising monkey variable regions and human constant regions. Methods for producing primatized antibodies are known in the art. See e.g., U.S. Pat. Nos. 5,658,570; 5,681, 722; and 5,693,780, which are incorporated by reference in their entireties.

The variant antibodies of the disclosure can be bispecific antibodies. Bispecific antibodies are monoclonal, often human or humanized, antibodies that have binding specificities for at least two different antigens. Non-limiting examples of antigen targets of bispecific antibodies include a cell-surface protein, receptor, receptor subunit, tissue-specific antigen, virally derived protein, virally encoded envelope protein, bacterially derived protein, or bacterial surface protein, etc.

The variant antibodies of the disclosure can be dual variable domain ("DVD") immunoglobulins ("DVD-Ig") (see, Gu & Ghayur, 2012, Methods in Enzymology 502:25-41, incorporated by reference herein in its entirety). A DVD-Ig combines the target-binding variable domains of two monoclonal antibodies via linkers to create a tetravalent, dual-targeting single agent. Suitable linkers for use in the light chains of the DVDs of the present disclosure include those identified on Table 2.1 on page 30 of Gu & Ghayur, 2012, Methods in Enzymology 502:25-41, incorporated by reference herein: the short κ chain linkers ADAAP (murine) and TVAAP (human); the long κ chain linkers ADAAPT-VSIFP (murine) and TVAAPSVFIFPP (human); the short λ chain linker QPKAAP (human); the long λ chain linker QPKAAPSVTLFPP (human); the GS-short linker GGSGG, the GS-medium linker GGSGGGGSG, and the GS-long linker GGSGGGGSGGGGS (all GS linkers are murine and human). Suitable linkers for use in the heavy chains of the DVDs of the present disclosure include those identified on Table 2.1 on page 30 of Gu & Ghayur, 2012, Methods in Enzymology 502:25-41, incorporated by reference herein: the short linkers AKTTAP (murine) and ASTKGP (human); the long linkers AKTTAPSVYPLAP (murine) and ASTK-GPSVFPLAP (human); the GS-short linker GGGGSG, the GS-medium linker GGGGSGGGGS, and the GS-long linker GGGGSGGGGSGGGG (all GS linkers are murine and human). Preferably human linkers are used for human or humanized DVD-Igs.

In the variant polypeptides of the present disclosure, the DVD-Ig can be directed towards two different targets. The targets can be selected from EGFR, HER2, ErbB3, or any other target described in Tariq et al., U.S. Patent Application Publication No. 2011/0044980, published Feb. 24, 2011 (incorporated by reference herein in its entirety).

Target binding domains of DVD immunoglobulins are typically arranged in tandem, with one variable domain stacked on top of another to form inner and outer Fv domains.

The variant antibodies of the disclosure include derivatized antibodies. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein (see Section 4.5 for a discussion of antibody conjugates), etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using Ambrx technology (See, e.g., Wolfson, 2006, Chem. Biol. 13:1011-2).

4.2.1. Targets of Fc Variant Antibodies

Virtually any antigen may be targeted by antibodies of the disclosure, including but not limited to proteins, subunits, domains, motifs, and/or epitopes belonging to the following list of target antigens, which includes both soluble factors such as cytokines and membrane-bound factors, including transmembrane receptors: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAM8, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, DNase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor 10a, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein 10b/IIIa (GP 10b/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGD2, PIN, PLA2, placental alkaline phosphatase (PLAP), PlGF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta RI (ALK-5), TGF-beta RII, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DcTRAIL R2TNFRH2), TNFRST23 (DcTRAIL R1TNFRH1), TNFRSF25 (DR3 Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3 Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, uPAR, uPAR-1, Urokinase, VCAM, VCAM-1, VECAD, VE-Cadherin, VE-cadherin-2, VEFGR-1 (flt-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factors.

An antibody of the disclosure, comprising the variant Fc domains described herein, can include the CDR sequences or the variable domain sequences of a known "parent" antibody. In some embodiments, the parent antibody and the antibody of the disclosure can share similar or identical sequences except for modifications to the Fc domain as disclosed herein.

For example, a parent antibody can be substantially similar to rituximab (Rituxan®, IDEC/Genentech/Roche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT/US2003/040426, entitled "Immunoglobulin Variants and Uses Thereof"). A number of antibodies that target members of the family of epidermal growth factor receptors, including EGFR (ErbB-1), Her2/neu (ErbB-2), Her3 (ErbB-3), Her4 (ErbB-4), may benefit from the Fc polypeptides of the present invention. For example the Fc polypeptides of the present invention may find use in an antibody that is substantially similar to trastuzumab (Herceptin®, Genentech) (see for example U.S. Pat. No. 5,677,171), a humanized anti-Her2/neu antibody approved to treat breast cancer; pertuzumab (rhuMab-2C4, Omnitarg™), currently being developed by Genentech; an anti-Her2 antibody described in U.S. Pat. No. 4,753,894; cetuximab (Erbitux®, Imclone) (U.S. Pat. No. 4,943,533; PCT WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Ser. No. 10/172,317), currently being developed by Genmab; 425, EMD55900, EMD62000, and EMD72000 (Merck KGaA) (U.S. Pat. No. 5,558,864; Murthy et al. 1987, Arch. Biochem. Biophys. 252:549-60; Rodeck et al., 1987, J. Cell Biochem. 35:315-20; Kettleborough et al., 1991, Protein Eng. 4:773-83); ICR62 (Institute of Cancer Research) (PCT WO 95/20045; Modjtahedi et al., 1993, J. Cell Biophys. 1993, 22:129-46; Modjtahedi et al., 1993, Br. J. Cancer, 67:247-53; Modjtahedi et al., 1996, Br. J. Cancer, 73:228-35; Modjtahedi et al., 2003, Int. J. Cancer, 105:273-80); TheraCIM hR3 (YM Biosciences, Canada and Centro de Immunologia Molecular, Cuba (U.S. Pat. No. 5,891,996; U.S. Pat. No. 6,506,883; Mateo et al., 1997, Immunotechnology 3:71-81); mAb-806 (Ludwig Institute for Cancer Research, Memorial Sloan-Kettering) (Jungbluth et al., 2003, Proc. Natl. Acad. Sci. 100:639-44); KSB-102 (KS Biomedix); MR1-1 (IVAX, National Cancer Institute) (PCT WO 0162931A2); and SC100 (Scancell) (PCT WO 01/88138). In another preferred embodiment, the Fc polypeptides of the present invention may find use in alemtuzumab (Campath®, Millenium), a humanized monoclonal antibody currently approved for treatment of B-cell chronic lymphocytic leukemia. The Fc polypeptides of the present invention may find use in a variety of antibodies or Fc fusions that are substantially similar to other clinical products and candidates, including but not limited to muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, abciximab (ReoPro®), developed by Centocor/Lilly, basiliximab (Simulect®), developed by Novartis, palivizumab (Synagis®), developed by MedImmune, infliximab (Remicade®), an anti-TNFalpha antibody developed by Centocor, adalimumab (Humira®), an anti-TNFalpha antibody developed by Abbott, Humicade™ an anti-TNFalpha antibody developed by Celltech, ABX-CBL, an anti-CD147 antibody developed by Abgenix, ABX-IL8, an anti-IL8 antibody developed by Abgenix, ABX-MA1, an anti-MUC18 antibody developed by Abgenix, Pemtumomab (R1549, 90Y-muHMFG1), an anti-MUC1 In development by Antisoma, Therex (R1550), an anti-MUC1 antibody developed by Antisoma, AngioMab (AS1405), developed by Antisoma, HuBC-1, developed by Antisoma, Thioplatin (AS1407) developed by Antisoma, Antegren® (natalizumab), an anti-alpha-4-beta-1 (VLA-4) and alpha-4-beta-7 antibody developed by Biogen, VLA-1 mAb, an anti-VLA-1 integrin antibody developed by Biogen, LTBR mAb, an anti-lymphotoxin beta receptor (LTBR) antibody developed by Biogen, CAT-152, an anti-TGF-β2 antibody developed by Cambridge Antibody Technology, J695, an anti-IL-12 antibody developed by Cambridge Antibody Technology and Abbott, CAT-192, an anti-TGFβ1 antibody developed by Cambridge Antibody Technology and Genzyme, CAT-213, an anti-Eotaxin1 antibody developed by Cambridge Antibody Technology, LymphoStat-B™ an anti-Blys antibody developed by Cambridge Antibody Technology and Human Genome Sciences Inc., TRAIL-R1 mAb, an anti-TRAIL-R1 antibody developed by Cambridge Antibody Technology and Human Genome Sciences, Inc., Avastin™ (bevacizumab, rhuMAb-VEGF), an anti-VEGF antibody developed by Genentech, an anti-HER receptor family antibody developed by Genentech, Anti-Tissue Factor (ATF), an anti-Tissue Factor antibody developed by Genentech, Xolair™ (Omalizumab), an anti-IgE antibody developed by Genentech, Raptiva™ (Efalizumab), an anti-CD11a antibody developed by Genentech and Xoma, MLN-02 Antibody (formerly LDP-02), developed by Genentech and Millenium Pharmaceuticals, HuMax CD4, an anti-CD4 antibody developed by Genmab, HuMax-IL15, an anti-IL15 antibody developed by Genmab and Amgen, HuMax-Inflam, developed by Genmab and Medarex, HuMax-Cancer, an anti-Heparanase I antibody developed by Genmab and Medarex and Oxford GcoSciences, HuMax-Lymphoma, developed by Genmab and Amgen, HuMax-TAC, developed by Genmab, IDEC-131, and anti-CD40L antibody developed by IDEC Pharmaceuticals, IDEC-151 (Clenoliximab), an anti-CD4 antibody developed by IDEC Pharmaceuticals, IDEC-114, an anti-CD80 antibody developed by IDEC Pharmaceuticals, IDEC-152, an anti-CD23 developed by IDEC Pharmaceuticals, anti-macrophage migration factor (MIF) antibodies developed by IDEC Pharmaceuticals, BEC2, an anti-idiotypic antibody developed by Imclone, IMC-1C11, an anti-KDR antibody developed by Imclone, DC101, an anti-flk-1 antibody developed by Imclone, anti-VE cadherin antibodies developed by Imclone, CEA-Cide™ (labetuzumab), an anti-carcinoembryonic antigen (CEA) antibody developed by Immunomedics, LymphoCide™ (Epratuzumab), an anti-CD22 antibody developed by Immunomedics, AFP-Cide, developed by Immunomedics, MyelomaCide, developed by Immunomedics, LkoCide, developed by Immunomedics, ProstaCide, developed by Immunomedics, MDX-010, an anti-CTLA4 antibody developed by Medarex, MDX-060, an anti-CD30 antibody developed by Medarex, MDX-070 developed by Medarex, MDX-018 developed by Medarex, Osidem™ (IDM-1), and anti-Her2 antibody developed by Medarex and Immuno-Designed Molecules, HuMax™-CD4, an anti-CD4 antibody developed by Medarex and Genmab, HuMax-IL15, an anti-IL15 antibody developed by Medarex and Genmab, CNTO 148, an anti-TNFα antibody developed by Medarex and Centocor/J&J, CNTO 1275, an anti-cytokine antibody developed by Centocor/J&J, MOR101 and MOR102, anti-intercellular adhesion molecule-1 (ICAM-1) (CD54) antibodies developed by MorphoSys, MOR201, an anti-fibroblast growth factor receptor 3 (FGFR-3) antibody developed by MorphoSys, Nuvion® (visilizumab), an anti-CD3 antibody developed by Protein Design Labs, HuZAF™, an anti-gamma interferon antibody developed by Protein Design Labs, Anti-α5β1 Integrin, developed by Protein Design Labs, anti-IL-12, developed by Protein Design Labs, ING-1, an anti-Ep-CAM antibody developed by Xoma, and MLN01, an anti-Beta2 integrin antibody developed by Xoma, all of the above-cited references in this paragraph are expressly incorporated herein by reference.

In one embodiment, the variants of the present invention are used for the treatment of autoimmune, inflammatory, or transplant indications. Target antigens and clinical products and candidates that are relevant for such diseases include but are not limited to anti-α4β7 integrin antibodies such as LDP-02, anti-beta2 integrin antibodies such as LDP-01, anti-complement (C5) antibodies such as 5G1.1, anti-CD2 antibodies such as BTI-322, MEDI-507, anti-CD3 antibodies such as OKT3, SMART anti-CD3, anti-CD4 antibodies such as IDEC-151, MDX-CD4, OKT4A, anti-CD11a antibodies, anti-CD14 antibodies such as IC14, anti-CD18 antibodies, anti-CD23 antibodies such as IDEC 152, anti-CD25 antibodies such as Zenapax, anti-CD40L antibodies such as 5c8, Antova, IDEC-131, anti-CD64 antibodies such as MDX-33, anti-CD80 antibodies such as IDEC-114, anti-CD147 antibodies such as ABX-CBL, anti-E-selectin antibodies such as CDP850, anti-gpIIb/IIIa antibodies such as ReoPro/Abcixima, anti-ICAM-3 antibodies such as ICM3, anti-ICE antibodies such as VX-740, anti-FcR1 antibodies such as MDX-33, anti-IgE antibodies such as rhuMab-E25, anti-IL-4 antibodies such as SB-240683, anti-IL-5 antibodies such as SB-240563, SCH55700, anti-IL-8 antibodies such as ABX-IL8, anti-interferon gamma antibodies, anti-TNF (TNF, TNFa, TNFα, TNF-alpha) antibodies such as CDP571, CDP870, D2E7, Infliximab, MAK-195F, and anti-VLA-4 antibodies such as Antegren.

Several of the antibodies described in this section have been subject to mutational analysis to improve their biological properties. Such mutant antibodies having desirable properties can be modified to incorporate the variant CH2 domains and Fc regions of the disclosure. US 2010/0266613 A1, for example, discloses variant $V_L$ and $V_H$ sequences of the anti-TNFα antibody adalimumab. The variant CH2 domains, variant CH3 domains and Fc regions of the disclosure can be incorporated into any of the variant anti-TNFα antibodies disclosed in US 2010/0266613 A1, which is incorporated by reference herein in its entirety. In some embodiments, the variant anti-TNFα antibody comprises one of more of the substitutions in Table 5 of US 2010/0266613, i.e., A25W, Q27R, Q27T, I29V, R30Q, and L33E in the VL chain. In other embodiments, the variant anti-TNFα antibody comprises a combination of substitutions from Table 10 of US 2010/0266613, i.e., I29T/A34G, N31T/A34G, R30Q/A34S, R30Q, Q27G/A34G, Q27H/

A34S, Q27R/A34S, G28S/A34S, N31T/A34S, or N31S/A34S in the $V_L$ chain, most preferably G28S/A34S. The stretch of amino acids spanning A25 through A34 is in bold, underlined font in Table 2 of US 2010/0266613.

4.3. Fc Fusion Proteins

In one embodiment, the polypeptides of the invention are Fc fusion proteins. Fc-based fusion proteins are typically composed of an immunoglobulin Fc domain that is directly linked to another peptide. As explained by Czajkowsky et al., 2012, EMBO Mol. Med. 4:1015-1028, the fusion partner can be any other proteinaceous molecule of interest, such as a ligand that activates upon interaction with a cell-surface receptor, a peptidic antigen (Ag) against a challenging pathogen or a 'bait' protein to identify binding partners assembled in a protein microarray. Most frequently, an Fc domain is fused to a polypeptide with therapeutic potential to endow the fusion with a number of additional beneficial biological and pharmacological properties. The presence of an Fc domain can markedly increase a protein's plasma half life, which prolongs its therapeutic activity owing to its interaction with the salvage neonatal Fc-receptor (FcRn; Roopenian & Akilesh, 2007, Nat. Rev. Immunol. 7:715-725), as well as to the slower renal clearance for larger sized molecules (Kontermann, 2011, Curr. Opin. Biotechnol. 22:868-876). The attached Fc domain also enables these molecules to interact with Fc-receptors (FcRs) found on immune cells (Nimmerjahn & Ravetch, 2008, Nat. Rev. Immunol. 8:34-47).

Accordingly, an Fc fusion combines the Fc region of an antibody, and thus its favorable effector functions and pharmacokinetics, with the target-binding region of a receptor, ligand, or some other protein or protein domain. The role of the latter is to mediate target recognition, and thus it is functionally analogous to the antibody variable region. Because of the structural and functional overlap of Fc fusions with antibodies, the discussion on antibodies in the present disclosure extends to Fc fusions unless indicated otherwise.

In exemplary embodiments, the Fc fusion partner is the extracellular domain ("ECD") of TNF receptor II; the first ECD of lymphocyte function-associated antigen 3 (LFA-3); the ECD of human cytotoxic T lymphocyte associated molecule-4 (CTLA-4); the C-terminus of the IL-1R accessory protein ligand binding region fused to the N-terminus of the IL-1RI ECD; peptide thrombopoietin (TPO) mimetic; ECD of CTLA-4 with the two amino acid substitutions L104E and A29Y; or ECDs of VEGF receptors 1 and 2.

An Fc fusion protein of the disclosure, comprising the variant Fc domains described herein, can be based on a known "parent" Fc fusion.

In some embodiments, the parent Fc fusion and the Fc fusion of the disclosure can share similar or identical sequences except for modifications to the Fc domain as disclosed herein.

Fc fusion proteins can also contain just a variant CH2 domain instead of a whole Fc region. Fusion proteins containing a variant CH2 domain can be used, for example, as a dimerization domain and/or to direct the fusion polypeptide to FcγRIIB. In one embodiment, the fusion partner is another Fc domain, such as an IgE Fc domain, creating a "tandem" Fc polypeptide. An IgG-IgE fusion polypeptide was shown to bind FcεR and FcγRIIB and shut down mast cell degranulation. See Cermerski et al., 2012, Immunol. Lett. 143:34-43

4.4. Nucleic Acids and Expression Systems

The present disclosure encompasses nucleic acid molecules and host cells encoding the Fc variant polypeptides of the disclosure.

A variant antibody of the disclosure that is an antibody can be prepared by recombinant expression of immunoglobulin light and heavy chain genes in a host cell. For example, to express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N. Y., 1989), Current Protocols in Molecular Biology (Ausubel, F. M. et al., eds., Greene Publishing Associates, 1989) and in U.S. Pat. No. 4,816,397.

In one embodiment, the Fc variant polypeptides are similar to their wild-type equivalents but for changes in their Fc domains. To generate nucleic acids encoding such Fc variant polypeptides, a DNA fragment encoding the Fc domain or a portion of the Fc domain of the wild-type antibody (referred to as the "wild-type Fc domain") can be synthesized and used as a template for mutagenesis to generate a polypeptide as described herein using routine mutagenesis techniques; alternatively, a DNA fragment encoding the polypeptide can be directly synthesized.

Once DNA fragments encoding wild-type Fc domains are obtained, these DNA fragments can be further manipulated by standard recombinant DNA techniques, for example, to convert the constant region genes to full-length antibody chain genes. In these manipulations, a CH2- or CH3-encoding DNA fragment is operatively linked to another DNA fragment encoding another protein, such as an antibody variable region or a flexible linker. The term "operatively linked," as used in this context, is intended to mean that the two DNA fragments are joined such that the amino acid sequences encoded by the two DNA fragments remain in-frame.

To express the Fc variant polypeptides of the disclosure, DNAs encoding partial or full-length light and heavy chains, obtained as described above, are inserted into expression vectors such that the genes are operatively linked to transcriptional and translational control sequences. In this context, the term "operatively linked" is intended to mean that a polypeptide gene is ligated into a vector such that transcriptional and translational control sequences within the vector serve their intended function of regulating the transcription and translation of the polypeptide gene. The expression vector and expression control sequences are chosen to be compatible with the expression host cell used. A variant antibody light chain gene and the antibody heavy chain gene can be inserted into separate vectors or, more typically, both genes are inserted into the same expression vector.

The polypeptide genes are inserted into the expression vector by standard methods (e.g., ligation of complementary restriction sites on the polypeptide gene fragment and vector, or blunt end ligation if no restriction sites are present). Prior to insertion of the variant Fc domain sequences, the expression vector can already carry antibody variable region sequences. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (See, e.g., U.S. Pat. Nos. 4,399,216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the polypeptides of the disclosure in either prokaryotic or eukaryotic host cells. In certain embodiments, expression of polypeptides is performed in eukaryotic cells, e.g., mammalian host cells, for optimal secretion of a properly folded and immunologically active polypeptide. Exemplary mammalian host cells for expressing the recombinant polypeptides of the disclosure include Chinese Hamster Ovary (CHO cells) (including DHFR⁻ CHO cells, described in Urlaub and Chasin, 1980, Proc. Natl. Acad. Sci. 77:4216-4220, used with a DHFR selectable marker, e.g., as described in Kaufman and Sharp, 1982, J. Mol. Biol. 159:601-621), NS0 myeloma cells, COS cells, 293 cells and SP2/0 cells. When recombinant expression vectors encoding polypeptide genes are introduced into mammalian host cells, the polypeptides are produced by culturing the host cells for a period of time sufficient to allow for expression of the polypeptide in the host cells or secretion of the polypeptide into the culture medium in which the host cells are grown. Polypeptides can be recovered from the culture medium using standard protein purification methods. Host cells can also be used to produce portions of intact polypeptides, such as Fab fragments or scFv molecules. It is understood that variations on the above procedure are within the scope of the present disclosure.

Recombinant DNA technology can also be used to remove some or all of the DNA encoding either or both of the light and heavy chains that is not necessary for binding to antigen. The molecules expressed from such truncated DNA molecules are also encompassed by the polypeptides of the disclosure.

In some embodiments, polypeptides of the disclosure can be bifunctional antibodies. Such antibodies, in which one heavy and one light chain are specific for one antigen and the other heavy and light chain are specific for a second antigen, can be produced by crosslinking an antibody of the disclosure to a second antibody by standard chemical crosslinking methods. Bifunctional antibodies can also be made by expressing a nucleic acid engineered to encode a bifunctional antibody.

In certain embodiments, dual specific antibodies, i.e. antibodies that bind one antigen and a second, unrelated antigen using the same binding site, can be produced by mutating amino acid residues in the light chain and/or heavy chain CDRs. Exemplary second antigens include a proinflammatory cytokine (such as, for example, lymphotoxin, interferon-γ, or interleukin-1). Dual specific polypeptides can be produced, e.g., by mutating amino acid residues in the periphery of the antigen binding site (See, e.g., Bostrom et al., 2009, Science 323:1610-1614). Dual functional polypeptides can be made by expressing a nucleic acid engineered to encode a dual specific polypeptide.

Polypeptides of the disclosure can also be produced by chemical synthesis (e.g., by the methods described in Solid Phase Peptide Synthesis, $2^{nd}$ ed., 1984, The Pierce Chemical Co., Rockford, Ill.). Polypeptides can also be generated using a cell-free platform (see, e.g., Chu et al., Biochemia No. 2, 2001 (Roche Molecular Biologicals)).

Methods for recombinant expression of Fc fusion proteins are described in Flanagan et al., Methods in Molecular Biology, vol. 378: Monoclonal Antibodies: Methods and Protocols.

Once a polypeptide of the disclosure has been produced by recombinant expression, it can be purified by any method known in the art for purification of an immunoglobulin molecule, for example, by chromatography (e.g., ion exchange, affinity, particularly by affinity for antigen after Protein A or Protein G selection, and sizing column chromatography), centrifugation, differential solubility, or by any other standard technique for the purification of proteins. Further, the polypeptides of the present disclosure or fragments thereof can be fused to heterologous polypeptide sequences described herein or otherwise known in the art to facilitate purification.

Once isolated, a polypeptide can, if desired, be further purified, e.g., by high performance liquid chromatography (See, e.g., Fisher, Laboratory Techniques In Biochemistry And Molecular Biology (Work and Burdon, eds., Elsevier, 1980)), or by gel filtration chromatography on a Superdex™ 75 column (Pharmacia Biotech AB, Uppsala, Sweden).

4.5. Biological Activity of Fc Variant Polypeptides

Due to the incorporation of amino acid substitutions in the Fc region, the polypeptides of the disclosure display altered binding to C1q and/or enhanced activation of complement dependent cytotoxicity, compared to a control polypeptide. The control polypeptide can have a wild-type CH2 (or wild-type Fc) domain and/or have a sequence that is identical to the polypeptide of the disclosure but for the single or double amino acid substitution from FIG. 9.

Binding to C1q can be assayed in vitro as described in Idusogie et al., 2000, J Immunol 164:4178-4184. In some aspects, the variant polypeptides of the disclosure exhibit increased affinity to C1q. The affinity can be increased by at least about 10%, 20%, 30%, 40%, 50%, 60%, 70%, 80%, 90%, or by about 100%, 200%, 300%, 400%, 500%, 1000% or even greater, as measured in vitro. In some embodiments, the percent affinity increase ranges between any of the foregoing values (e.g., about 10%-100%, about 30%-80%, about 50%-200%, about 100%-500%, etc.).

Enhanced activation of CDC can be assayed using known methods, including the commercially available CytoTox-Glo Cytotoxicity Assay (Promega, Madison, Wis.). The CytoTox-Glo Cytotoxicity Assay uses a luminogenic peptide substrate to measure dead-cell protease activity, which is released from cells that have lost membrane integrity. The luminogenic peptide cannot cross the intact membrane of live cells and does not generate any appreciable signal from the live-cell population. Upon cell death, the peptide is released and its luminescent signal can be measured. An exemplary protocol using the CytoTox-Glo Cytotoxicity Assay is described in Example 4.

Another method used to measure CDC is described in U.S. Pat. No. 7,994,290, and makes use of a target cell labeled (e.g., with a radioisotope, a fluorescent substance, or a dye). The labeled target cell is placed into contact with an antibody and a sample containing a complement component. Upon injury of the target cell via CDC, the labeled substance is released and can be measured.

In some aspects, the variant polypeptides of the disclosure exhibit improved (i.e., reduced) $EC_{50}$ values in a CDC assay. The $EC_{50}$ values can be improved by at least about 50%, 60%, 70%, 80%, 90%, or by about 100%, 200%, 300%, 400%, 500%, 1,000%, 2,500% or even greater, for example by about 5,000%. In some embodiments, the improvement in $EC_{50}$ value ranges between any of the foregoing values (e.g., about 200%-5,000%, about 100%-2,500%, about 1,000%-2,500%, about 500%-5,000%, etc.).

In other aspects, the variant polypeptides of the disclosure exhibit an increase in maximal lysis elicited in a CDC assay. The maximal lysis can be improved by at least about 10%, at least 20%, at least 30%, at least 40%, at least 50%, or even greater, for example by about 60%. In some embodiments, the improvement in maximal lysis ranges between any of the foregoing values (e.g., about 10%-60%, about 20%-60%, about 30%-50%, about 40%-60%, etc.).

4.6. Polypeptide Conjugates

The polypeptides of the disclosure include polypeptide conjugates that are modified, e.g., by the covalent attachment of any type of molecule to the polypeptide, such that covalent attachment does not interfere with binding to antigen.

In certain aspects, a polypeptide of the disclosure can be conjugated to an effector moiety or a label. The term "effector moiety" as used herein includes, for example, antineoplastic agents, drugs, toxins, biologically active proteins, for example enzymes, antibody or antibody fragments, synthetic or naturally occurring polymers, nucleic acids (e.g., DNA and RNA), radionuclides, particularly radioiodide, radioisotopes, chelated metals, nanoparticles and reporter groups such as fluorescent compounds or compounds which can be detected by NMR or ESR spectroscopy.

In one example, polypeptides can be conjugated to an effector moiety, such as a cytotoxic agent, a radionuclide or drug moiety to modify a given biological response. The effector moiety can be a protein or polypeptide, such as, for example and without limitation, a toxin (such as abrin, ricin A, *Pseudomonas* exotoxin, or *Diphtheria* toxin), a signaling molecule (such as α-interferon, β-interferon, nerve growth factor, platelet derived growth factor or tissue plasminogen activator), a thrombotic agent or an anti-angiogenic agent (e.g., angiostatin or endostatin) or a biological response modifier such as a cytokine or growth factor (e.g., interleukin-1 (IL-I), interleukin-2 (IL-2), interleukin-6 (IL-6), granulocyte macrophage colony stimulating factor (GM-CSF), granulocyte colony stimulating factor (G-CSF), or nerve growth factor (NGF)).

In another example the effector moieties can be cytotoxins or cytotoxic agents. Examples of cytotoxins and cytotoxic agents include taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector moieties also include, but are not limited to, antimetabolites (e.g. methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C5 and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and anti-mitotic agents (e.g., vincristine and vinblastine).

Other effector moieties can include radionuclides such as, but not limited to, $^{111}$In and $^{90}$Y, Lu$^{177}$, Bismuth$^{213}$, Californium$^{252}$, Iridium$^{192}$ and Tungsten$^{188}$/Rhenium$^{188}$ and drugs such as, but not limited to, alkylphosphocholines, topoisomerase I inhibitors, taxoids and suramin.

Techniques for conjugating such effector moieties to polypeptides are well known in the art (See, e.g., Hellstrom et al., Controlled Drug Delivery, 2nd Ed., at pp. 623-53 (Robinson et al., eds., 1987)); Thorpe et al., 1982, Immunol. Rev. 62:119-58 and Dubowchik et al., 1999, Pharmacology and Therapeutics 83:67-123).

In one example, the polypeptide is fused via a covalent bond (e.g., a peptide bond), through the polypeptide's N-terminus or the C-terminus or internally, to an amino acid sequence of another protein (or portion thereof; for example, at least a 10, 20 or 50 amino acid portion of the protein). The polypeptide can linked to the other protein at the N-terminus of the Fc domain of the polypeptide. Recombinant DNA procedures can be used to create such fusions, for example as described in WO 86/01533 and EP0392745. In another example the effector molecule can increase half life in vivo, and/or enhance the delivery of a polypeptide across an epithelial barrier to the immune system. Examples of suitable effector molecules of this type include polymers, albumin, albumin binding proteins or albumin binding compounds such as those described in WO 2005/117984.

In certain aspects, a polypeptide is conjugated to a small molecule toxin. In certain exemplary embodiments, a polypeptide of the disclosure is conjugated to a dolastatin or a dolastatin peptidic analogs or derivatives, e.g., an auristatin (U.S. Pat. Nos. 5,635,483 and 5,780,588). The dolastatin or auristatin drug moiety may be attached to the polypeptide through its N (amino) terminus, C (carboxyl) terminus or internally (WO 02/088172). Exemplary auristatin embodiments include the N-terminus linked monomethylauristatin drug moieties DE and DF, as disclosed in U.S. Pat. No. 7,498,298, which is hereby incorporated by reference in its entirety (disclosing, e.g., linkers and methods of preparing monomethylvaline compounds such as MMAE and MMAF conjugated to linkers).

In other exemplary embodiments, small molecule toxins include but are not limited to calicheamicin, maytansine (U.S. Pat. No. 5,208,020), trichothene, and CC1065. In one embodiment of the disclosure, the polypeptide is conjugated to one or more maytansine molecules (e.g., about 1 to about 10 maytansine molecules per polypeptide molecule). Maytansine may, for example, be converted to May-SS-Me which may be reduced to May-SH3 and reacted with an polypeptide (Chari et al., 1992, Cancer Res. 52:127-131) to generate a maytansinoid-polypeptide or maytansinoid-Fc fusion conjugate. Structural analogues of calicheamicin that can also be used include but are not limited to $\gamma_1^1$, $\gamma_3^1$, $\gamma_3^1$ N-acetyl-$\gamma_1^1$, PSAG, and $\theta_1^1$, (Hinman et al., 1993, Cancer Res. 53:3336-3342; Lode et al., 1998, Cancer Res. 58:2925-2928; U.S. Pat. Nos. 5,714,586; 5,712,374; 5,264,586; 5,773,001).

Polypeptides of the disclosure can also be conjugated to liposomes for targeted delivery (See, e.g., Park et al., 1997, Adv. Pharmacol. 40:399-435; Marty & Schwendener, 2004, Methods in Molecular Medicine 109:389-401).

In one example polypeptides of the present disclosure can be attached to poly(ethyleneglycol) (PEG) moieties. In one particular example the polypeptide is an antibody fragment and the PEG moieties can be attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See, for example, U.S. Pat. No. 5,219,996. Multiple sites can be used to attach two or more PEG molecules. PEG moieties can be covalently linked through a thiol group of at least one cysteine residue located in the antibody fragment. Where a thiol group is used as the point of attachment, appropriately activated effector moieties (for example, thiol selective derivatives such as maleimides and cysteine derivatives) can be used.

The word "label" when used herein refers to a detectable compound or composition which can be conjugated directly or indirectly to a polypeptide of the disclosure. The label can itself be detectable (e.g., radioisotope labels or fluorescent labels) or, in the case of an enzymatic label, can catalyze chemical alteration of a substrate compound or composition which is detectable. Useful fluorescent moieties include, but are not limited to, fluorescein, fluorescein isothiocyanate, rhodamine, 5-dimethylamine-1-naphthalenesulfonyl chloride, phycoerythrin and the like. Useful enzymatic labels include, but are not limited to, alkaline phosphatase, horseradish peroxidase, glucose oxidase and the like.

4.7. Pharmaceutical Compositions and Therapeutic Methods

The variant polypeptides of the disclosure are useful in treating a variety of immune diseases and cancers. The specific indication or indications that are suitable for treatment using an Fc variant polypeptide will depend on the sequence and/or properties of the non-Fc or portion of the Fc variant polypeptide, and can be readily determined by a person of ordinary skill in the art. Exemplary embodiments are set forth below.

In one embodiment, a variant polypeptide of the disclosure is an anti-CD40 antibody and is used to treat a CD40-expressing cancer, such as chronic lymphocytic leukemia, Burkitt's lymphoma, multiple myeloma, a T cell lymphoma, Non-Hodgkin's Lymphoma, Hodgkin's Disease, Waldenstrom's macroglobulinemia or Kaposi's sarcoma.

In another embodiment, a variant polypeptide of the disclosure is an anti-CD20 antibody and is used to treat rheumatoid arthritis or multiple sclerosis.

In another embodiment, a variant polypeptide of the disclosure is an anti-CD25 antibody and is used to treat multiple sclerosis, psoriasis, asthma, uveitis, ocular inflammation or human T cell leukemia virus-1 associated T-cell leukemia or to prevent organ transplant rejection.

In another embodiment, a variant polypeptide of the disclosure is an anti-TNFα antibody and is used to treat rheumatoid arthritis, psoriasis or Crohn's disease.

In another embodiment, a variant polypeptide of the disclosure is an anti-IL-6 receptor antibody and is used to treat rheumatoid arthritis or Castleman's Disease.

In another embodiment, a variant polypeptide of the disclosure is an anti-α4-integrin antibody and is used to treat multiple sclerosis.

In another embodiment, a variant polypeptide of the disclosure is an anti-IL-1 antibody and is used to treat Cryopyrin-Associated Periodic Syndromes ("CAPS").

In another embodiment, a variant polypeptide of the disclosure is an anti-BAFF antibody and is used to treat systemic lupus erythmatosis or allergy.

The disclosure provides methods of treating any of the foregoing diseases in a patient in need thereof, comprising: administering to the patient an appropriate polypeptide of the disclosure in a therapeutically effective dose.

As used herein, a "therapeutically effective" amount of a polypeptide can be administered as a single dose or over the course of a therapeutic regimen, e.g., over the course of a week, two weeks, three weeks, one month, three months, six months, one year, or longer.

The dosage of a polypeptides of the disclosure to be administered of will vary according to the particular antigen specificity, the type of autoimmune or inflammatory disease, the subject, and the nature and severity of the disease, the physical condition of the subject, the therapeutic regimen (e.g., whether a combination therapeutic agent is used), and the selected route of administration; the appropriate dosage can be readily determined by a person skilled in the art.

For the treatment and/or prophylaxis of autoimmune or inflammatory disease in humans and animals, pharmaceutical compositions comprising polypeptides can be administered to patients (e.g., human subjects) at therapeutically or prophylactically effective dosages (e.g., dosages which result in inhibition of an autoimmune or inflammatory disease and/or relief of autoimmune or inflammatory disease symptoms) using any suitable route of administration, such as injection and other routes of administration known in the art for antibody-based clinical products.

It will be recognized by one of skill in the art that the optimal quantity and spacing of individual dosages of a polypeptide of the disclosure will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

According to the present disclosure, treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom the polypeptide of the disclosure is administered is preferably a mammal such as a non-primate (e.g., cow, pig, horse, cat, dog, rat, etc.) or a primate (e.g., monkey or human). In certain embodiments, the subject or patient is a human. In certain aspects, the human is a pediatric patient. In other aspects, the human is an adult patient.

Compositions comprising a polypeptide of the disclosure are provided herein. The compositions will typically be supplied as part of a sterile, pharmaceutical composition that will normally include a pharmaceutically acceptable carrier. This composition can be in any suitable form (depending upon the desired method of administering it to a patient).

Pharmaceutical compositions can be conveniently presented in unit dose forms containing a predetermined amount of a polypeptide of the disclosure per dose. Such a unit can contain for example but without limitation 5 mg to 5 g, for example 10 mg to 1 g, or 20 to 50 mg, 40 mg to 100 mg, or 50 mg to 300 mg. Pharmaceutically acceptable carriers for use in the disclosure can take a wide variety of forms depending, e.g., on the condition to be treated or route of administration.

Therapeutic formulations of the polypeptides of the disclosure can be prepared for storage as lyophilized formulations or aqueous solutions by mixing the polypeptide having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Nonionic surfactants can be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents. Further formulations suitable for the polypeptides of the disclosure are disclosed in U.S. Pat. App. No. 2004/0033228 A1, the contents of which are incorporated by reference herein in their entirety.

5. EXAMPLES

Example 1

Construction of Vectors for Expression and Cell Surface Display of Hu1D10 Library Hu1D10 is a humanized IgG1/kappa anti-HLA-DR β chain allele antibody (Kostelny et al., 2001, Int. J. Cancer 93:556-565). Expression and cell surface display of a library of Hu1D10 constructs was achieved using derivatives of the expression vector pYA206, itself a derivative of vector pYA104 (Akamatsu et al., 2007, J. Immunol. Methods 327:40-52). Vector pYA104 is an EBV-derived plasmid for display of full-length IgG1 antibodies on the surface of HEK 293c18 cells via a GPI anchor. Vectors that were used in the examples described herein bear the following modifications: 1) the human C lambda constant domain has been replaced with the human C kappa constant domain; 2) the glycosidylphosphatidylinositol linkage signal (GPI anchor) has been replaced with the transmembrane domain of the platelet-derived growth factor receptor (PDGF-R); 3) unique NotI and XhoI sites have been introduced upstream of the C kappa domain for cloning VL domains in frame with the C kappa constant domain; and 4) unique NgoMIV and SacI sites have been introduced upstream of IgG1 for cloning VH domains in-frame with the IgG1 constant domains. The vectors contained the EBNA-1 gene and oriP from Epstein-Barr virus, which allowed replication in mammalian cells as an episome. Mammalian cell transfectants were selected with the puromycin resistance gene under control of the SV40 promoter. The CMV promoter and internal ribosome entry site ("IRES") allowed for expression of the displayed antibody light and heavy chains. The expressed antibody was tethered to the cell membrane via the PDGF-R transmembrane domain fused to the end of the IgG1 constant domain. The pUC origin of replication and ampicillin resistance gene allowed the plasmid to be propagated in E. coli.

The Hu1D10 VL fragment was PCR-amplified and digested with NotI and XhoI. The Hu1D10 VH fragment was PCR-amplified and digested with NgoMIV and SacI. Both fragments were then cloned into plasmid pYA206 to create plasmid pYA206-Hu1D10. For expression of soluble IgG1 antibody, the PDGF-R transmembrane domain was removed by digestion with ClaI and BstBI, followed by ligation of the compatible cohesive ends, as described (Akamatsu et al., 2007, J. Immunol. Methods 327:40-52).

The expression vector pHybE (U.S. Pat. No. 8,187,836) is an episomal vector for high protein production in mammalian cells (e.g., HEK 293-6E cells) expressing the Epstein-Barr virus nuclear antigen ("EBNA"). This plasmid contains the oriP from Epstein-Barr virus, which allows replication in mammalian cells as an episome. The EF-1a promoter allows for expression of the antibody light or heavy chains. The pUC origin of replication and ampicillin resistance gene allow the plasmid to be propagated in E. coli.

The Hu1D10 VL fragment was amplified by PCR, digested with NruI and BsiWI and cloned into pHybE-hCk (U.S. Pat. No. 8,187,836) to create plasmid pHybE-Hu1D10-Ck. The Hu1D10 VH fragment was amplified by PCR, digested with NruI and SalI and cloned into pHybE-hCg1, z, non-a (U.S. Pat. No. 8,187,836) to create plasmid pHybE-Hu1D10-IgG1.

Example 2

Mutagenesis of the Fc Region of the Human IgG1 Heavy Chain Gene

The CH2 domain of the Hu1D10-IgG1 antibody was subjected to comprehensive mutational analysis using methodology similar to that described by Forsyth et al., 2013, mAbs 5:523-532, to identify mutants that had increased affinity to C1q as compared to wild-type Hu1D10-IgG1. A synthetic gene sequence encoding a portion of the CH1 domain, as well as the hinge, CH2 and CH3 domains of human IgG1 (z, non-a) was constructed by a commercial gene synthesis supplier (DNA 2.0, Menlo Park, Calif.). Single amino acid mutants of the template sequence were created by NNK mutagenesis (DNA 2.0). The resulting AgeI-BglII fragments were cloned into plasmid pYA206-Hu1D10, which was then digested with ClaI and BstBI, followed by ligation of the compatible cohesive ends to remove the PDGF-R transmembrane domain.

Combination mutants were synthesized by a commercial gene synthesis supplier (GeneArt/Life Technologies, Grand Island, N.Y.). The resulting SalI-NotI fragments were cloned into plasmid pHybE-Hu1D10-IgG1.

Example 3

Expression and Purification of Wild-Type and Mutant Human IgG1 Antibodies

Cell Culture:

Human kidney cell line HEK 293c18 (Stanford University, Stanford, Calif.) was maintained in DMEM (HyClone, Logan, Utah) containing 10% Fetal Bovine Serum (FBS) (Gibco/Life Technologies, Grand Island, N.Y.), 0.25 mg/ml G418 (Mediatech, Manassas, Va.) and 1% penicillin-streptomycin (HyClone)—hereinafter referred to as "293 medium"—at 37° C. in a 7.5% $CO_2$ incubator. For expression and purification of monoclonal antibodies after transient transfection, HEK 293c18 cells were incubated in DMEM containing 2% ultralow-IgG FBS (Gibco), 0.1 mM MEM non-essential amino acids (HyClone) and 2 mM L-glutamine (HyClone), hereinafter referred to as "low-IgG 293 medium."

Human kidney cell line HEK 293-6E (EBNA) (National Research Council, Ottawa, ON, Canada) was maintained in FreeStyle 293 media (Gibco) at 37° C. in an 8.0% $CO_2$ incubator, with shaking.

Transient Transfection:

HEK 293c18 cells were transiently transfected with the pYA206-Hu1D10 plasmid containing the light chain and a wild-type or mutant heavy chain in secreted form. Approximately $2.25 \times 10^7$ cells per transfection were inoculated in a T-175 flask in 50 ml of 293 medium and grown overnight to ~70% confluence. The next day, 48 µg of plasmid were combined with 3.0 ml of Hybridoma-SFM ("HSFM") (Gibco). In a separate tube, 120 µl of Lipofectamine 2000 reagent (Invitrogen/Life Technologies, Grand Island, N.Y.) and 3.0 ml of HSFM were combined and incubated for 5 minutes at room temperature. The 3.0 ml Lipofectamine 2000-HSFM mixture was mixed gently with the 3.0 ml DNA-HSFM mixture and incubated at room temperature for 20 minutes. The medium covering the HEK 293c18 cells was aspirated and replaced with low-IgG 293 medium, and then the lipofectamine-DNA complexes were added dropwise to the cells, and mixed gently by swirling. The cells were incubated for 5-7 days at 37° C. in a 7.5% $CO_2$ incubator before harvesting the supernatants.

HEK 293-6E cells were transiently co-transfected with the pHybE-Hu1D10-Ck light chain plasmid and a pHybE-Hu1D10-IgG1 wild-type or mutant heavy chain plasmid. The day before the transfection, the cells were split in FreeStyle 293 media and grown overnight to a density of $1.0 \times 10^6$ cells/ml on the day of transfection. The next day, 20

μg of heavy chain plasmid and 30 μg of light chain plasmid were added to 5.0 ml of FreeStyle 293 media, sterile-filtered, combined with 100 μg of PEI reagent (Polysciences, Warrington, Pa.), incubated at room temperature for 10 minutes and added to 100 ml of HEK 293-6E cells in a 500 ml flask. The flasks were placed on a shaker in an 8.0% $CO_2$ incubator at 37° C. After 4 hours, the cells were fed with 5 ml of 10% tryptone N1 (TekniScience, Terrebonne, QC, Canada) in FreeStyle 293 media. The cells were incubated for 4-5 days at 37° C. in an 8.0% $CO_2$ incubator with shaking prior to harvesting the supernatants.

ELISA:

To measure the amount of antibody present in culture supernatants, an ELISA was performed according to standard methods using goat anti-human IgG Fcγ fragment-specific antibody (Jackson ImmunoResearch Laboratories, West Grove, Pa.) as a capture reagent, goat anti-human kappa light chain HRP-conjugated antibody (Southern Biotechnology Associates, Birmingham, Ala.) as a detection reagent, and purified Hu1D10 as a standard. The plates were developed with TMB Substrate (BioFX Laboratories, Owings Mills, Md.) and absorbance at 650 nm was measured using a VERSAmax ELISA Microplate Reader (Molecular Devices, Sunnyvale, Calif.).

Antibody Purification:

For purification of antibody from transient transfections, culture supernatants were harvested by centrifugation and sterile filtered. Supernatants were passed over a HiTrap Protein G or Protein A column (GE Healthcare Bio-Sciences, Piscataway, N.J.) that was pre-equilibrated with PBS, pH 7.4. The column was washed with the same buffer, and bound antibody was eluted with 20 mM sodium citrate, pH 3.5. After neutralization by addition of 1/20 volume of 1 M Tris base, pooled fractions were dialyzed into PBS, pH 7.4, and then filter sterilized using 0.2 μm Millex-GV microfilters (EMD Millipore, Billerica, Mass.). The concentrations of the purified antibodies were determined by UV spectroscopy by measuring the absorbance at 280 nm (1 mg/ml=1.4 $A_{280}$).

SDS-PAGE:

Five μg samples of purified antibodies were analyzed by SDS-polyacrylamide gel electrophoresis (SDS-PAGE) under reducing or non-reducing conditions on NuPAGE 4-12% Bis-Tris gels (Novex/Life Technologies, Grand Island, N.Y.) and stained using SimplyBlue SafeStain (Novex) following the manufacturer's recommendations.

Size Exclusion Chromatography:

Twenty-five μg samples of purified antibodies were analyzed by size-exclusion chromatography ("SEC") using a TSKgel $G3000SW_{XL}$ column (Tosoh Bioscience, King of Prussia, Pa.) in 0.1 M $NaPO_4$, 0.1 M $Na_2SO_4$, pH 6.7.

Results:

The IgG1 Fc mutants were expressed as Hu1D10 antibodies, comprising the light and heavy chain variable regions of Hu1D10, the light chain constant region of human kappa, and the heavy chain constant regions of human IgG1, respectively. As described above, the wild-type plasmid or one of the various plasmids containing a mutated heavy chain was transiently transfected into HEK 293c18 cells for expression of Hu1D10 monoclonal antibodies. ELISA analysis of culture supernatants harvested 5-7 days after transient transfection indicated that the antibody expression level was typically about 5 μg/ml). Hu1D10 antibodies were purified by protein G affinity chromatography for a final yield of approximately 0.25-0.50 mg of IgG1 antibody.

Alternatively, the light chain plasmid and the wild-type or mutant heavy chain plasmid were transiently co-transfected into HEK 293-6E cells for expression of Hu1D10 monoclonal antibodies. ELISA analysis of culture supernatants harvested 4-5 days after transient transfection indicated that the antibody expression level was typically 50-150 μg/ml. Hu1D10 antibodies were purified by protein A affinity chromatography for a final yield of approximately 3-10 mg of IgG1 antibody.

Purified antibodies were characterized by SDS-PAGE under non-reducing and reducing conditions. SDS-PAGE analysis under non-reducing conditions indicated that the purified antibodies had a molecular weight of about 150-160 kD, while analysis under reducing conditions indicated that the purified antibodies comprised a heavy chain with a molecular weight of about 50 kD and a light chain with a molecular weight of about 25 kD.

Purified antibodies were further characterized by analytical SEC, which indicated that the purified antibodies gave rise to a single predominant peak consistent with that of an IgG monomer and contained less than 2% aggregated protein material.

Example 4

Characterization of the CDC Activity of Wild-Type and Mutant Human IgG1 Antibodies Cell Culture:

Human Burkitt's lymphoma cell line Raji (American Type Culture Collection, Manassas, Va.) was maintained in RPMI 1640 medium (HyClone) containing 10% heat-inactivated FBS (Gibco).

CDC Assay:

The complement-dependent cytotoxicity ("CDC") activity of Hu1D10 wild-type and mutant antibodies was measured with pooled normal human serum complement ("NHSC") and Raji cells as targets using the CytoTox-Glo Cytotoxicity Assay (Promega, Madison, Wis.). Raji cells were washed in CDC Assay Medium ("CDC-AM") (RPMI 1640, 10 mM HEPES, 0.1% BSA) and resuspended at a density of $5.0 \times 10^5$ cells/ml in CDC-AM. Hu1D10 wild-type and mutant antibodies were serially diluted in CDC-AM beginning at 150 μg/ml. NHSC (Quidel, San Diego, Calif.) was diluted 1:3.3 in CDC-AM. Raji cells (50 μl/well), serially diluted Hu1D10 antibody (50 μl/well), and diluted NHSC (50 μl/well) were combined in the wells of a Falcon TC-treated U-bottom plate (BD Biosciences, San Jose, Calif.) and incubated for 2 hours at 37° C. in a $CO_2$ incubator. Maximum release ("MR") was measured by adding 0.2% digitonin to target cells. Spontaneous release ("SR") was measured by incubating target cells in the absence of antibody. After 2 hours, CytoTox-Glo reagent (50 μl/well) was added to the plates and mixed for 1 minute on a rotary shaker. The plates were then incubated at room temperature for 15 minutes, after which the plates were gently centrifuged and the supernatants (100 μl/well) were transferred to a Microlite TCT flat-bottom plate (Thermo Scientific, Rochester, N.Y.). Luminescence was measured using a $VICTOR^3$ 1420 Multilabel Counter (PerkinElmer, Waltham, Mass.). The percent cytotoxicity was calculated using the formula [(Sample−SR)/(MR−SR)]×100.

Cytotoxicity data at multiple concentrations were generated for the wild-type and mutated antibodies, and sigmoidal dose-response curves were fit to the resulting data. Based on these curves, EC50 (effective concentration, 50%) and top (maximum percent lysis at the top plateau) values were calculated (Prism 6, GraphPad Software, La Jolla, Calif.). Within each assay, fold change values relative to the wild-type antibody were calculated for the EC50 and top values by dividing the EC50 and top values for each mutant by the EC50 and top values for the wild-type. Finally, for each mutant, the fold changes in EC50 and top were averaged across all experiments containing data for that mutant.

Figure 4A:
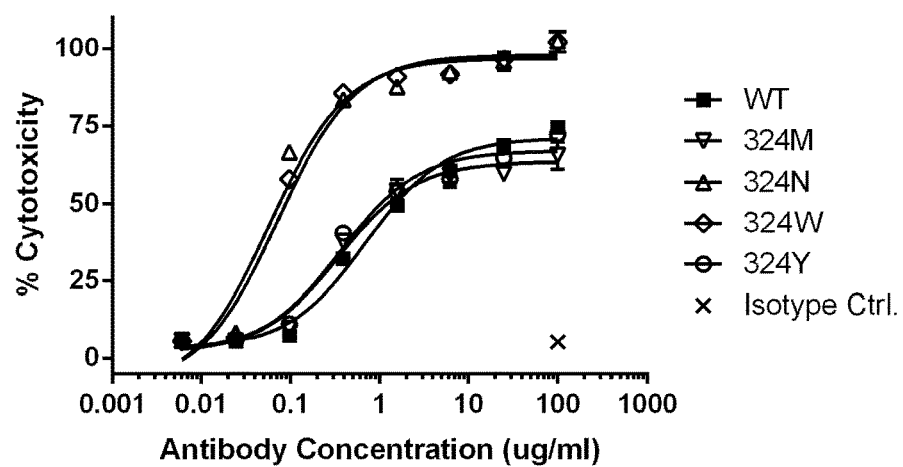
Figure 4B:
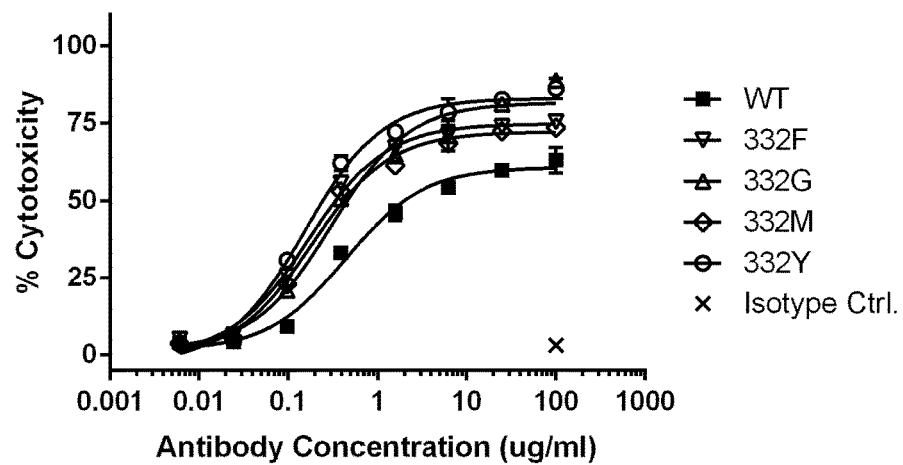
Figure 4C:
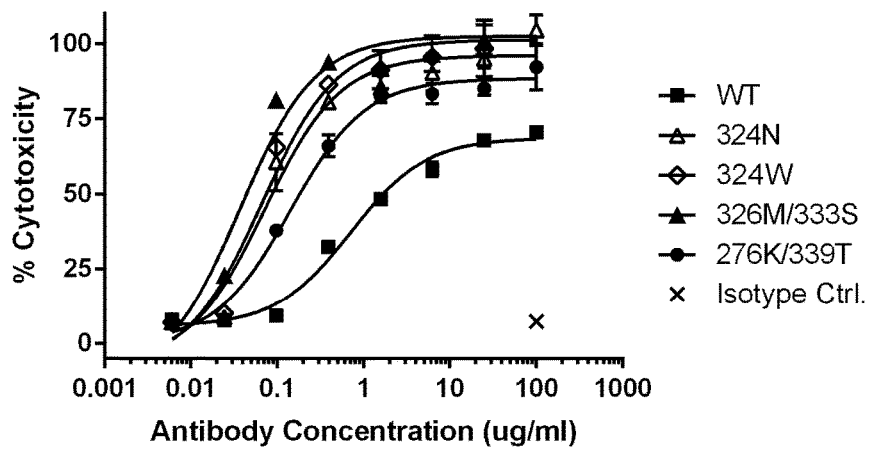
Figure 4D:
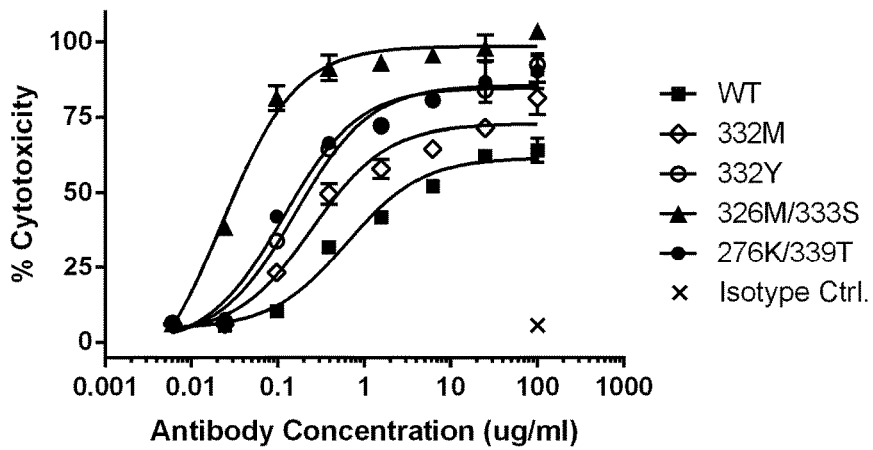

Results:

The relative CDC activity of Hu1D10 wild-type and various single mutant antibodies was determined as described above. The antibodies were expressed by transient transfection of HEK 293c18 cells and purified by protein G chromatography. Their CDC activity was confirmed using pooled NHSC and Raji cells as targets. The results of typical experiments are shown in FIGS. 4A-4D and summarized in FIG. 7. As shown in FIG. 4A, the Hu1D10-IgG1 single mutants S324N and S324W had substantially improved potency (EC50) and efficacy (maximum percent lysis) compared to the wild-type antibody, while the single mutants S324M and S324Y had comparable potency and efficacy to the wild-type antibody. As expected, an isotype control antibody had no CDC activity. Similarly, as shown in FIG. 4B, the Hu1D10-IgG1 single mutants I332F, I332G, I332M and I332Y had substantially improved potency and efficacy compared to the wild-type antibody, while an isotype control antibody had no CDC activity, as expected. As shown in FIG. 4C, when compared with Hu1D10-IgG1 antibodies containing described mutations, the Hu1D10-IgG1 single mutants S324N and S324W had improved potency and efficacy compared to the N276K/A339T double mutant (U.S. Pat. No. 7,994,290) and slightly reduced potency and similar efficacy compared to the K326M/E333S double mutant (Idusogie et al., 2001, J. Immunol. 166:2571-2575). As shown in FIG. 4D, the Hu1D10-IgG1 single mutant I332M had reduced potency and efficacy compared to the N276K/A339T double mutant, while the single mutant I332Y had comparable potency and efficacy to the N276K/A339T double mutant. The Hu1D10-IgG1 single mutants I332M and I332Y both had reduced potency and efficacy compared to the K326M/E333S double mutant. As summarized in FIG. 7, the fold-increase in the EC50 value of the mutants compared with wild-type Hu1D10-IgG1 antibody is ~1.5-fold for the single mutant I332G, ~2-fold for the single mutants S324M and S324Y, ~2.5-fold for the single mutants I332F and I332M, ~3.5-fold for the single mutant I332Y and ~10-11-fold for the single mutants S324N and S324W. As summarized in FIG. 7, the fold-increase in the maximum percent lysis is ~1.2-1.4-fold (i.e., ~20-40%) for the single mutants S324N, S324W, I332F, I332G, I332M and I332Y.

The relative CDC activity of Hu1D10 wild-type and various double mutant antibodies was also determined. As described above, the antibodies were expressed by transient transfection of HEK 293-6E cells, purified by protein A chromatography and their CDC activity was confirmed using pooled NHSC and Raji cells as targets. The results of a typical experiment are shown in FIG. 5 and summarized in FIG. 8. As shown in FIG. 5, the Hu1D10-IgG1 double mutants S324N/I332F, S324W/I332F, S324N/I332M, S324W/I332M, S324N/I332Y and S324W/I332Y all had substantially improved potency and improved efficacy compared to the wild-type antibody. As predicted from the literature (Lazar et al., 2006, Proc. Natl. Acad. Sci. 103: 4005-4010), the Hu1D10-IgG1 single mutant A330L had lower potency and efficacy compared to the wild-type antibody, while an isotype control antibody had no CDC activity, as expected. When compared with Hu1D10-IgG1 antibodies containing known mutations, the Hu1D10-IgG1 double mutants S324N/I332F, S324W/I332F, S324N/I332M and S324W/I332M had similar potency and efficacy compared to the S267E/H268F/S324T triple mutant (Moore et al., 2010, mAbs 2:181-189), and superior potency and efficacy compared to the H268F/S324T double mutant (Moore et al., 2010, mAbs 2:181-189) or the N276K/A339T double mutant (U.S. Pat. No. 7,994,290). Further, the Hu1D10-IgG1 double mutants S324N/I332Y and S324W/I332Y had superior potency and similar efficacy compared to the S267E/H268F/S324T triple mutant (Moore et al., 2010, mAbs 2:181-189). As summarized in FIG. 8, the average fold-increase in the EC50 value of the mutants compared with wild-type Hu1D10-IgG1 antibody is ~13-16-fold for the double mutants S324N/I332F, S324W/I332F, S324N/I332M and S324W/I332M, and ~20-23-fold for the double mutants S324N/I332Y and S324W/I332Y. As summarized in FIG. 8, the average fold-increase in the maximum percent lysis is ~1.3-1.4-fold (i.e., ~30-40%) for the double mutants S324N/I332F, S324W/I332F, S324N/I332M, S324W/I332M, S324N/I332Y and S324W/I332Y.

Example 5

Characterization of FcγRIIIA Binding of Wild-Type and Mutant Human IgG1 Antibodies FcγRIIIA ELISA:

The FcγRIIIA binding activity of Hu1D10 wild-type and mutant antibodies was measured by ELISA using a published method (Niwa et al., 2004, Clin. Cancer Res. 10:6248-6255). Nunc MaxiSorp plates (Thermo Scientific) were coated overnight at 4° C. with 100 µl/well of goat anti-6× histidine antibody (R&D Systems, Minneapolis, Minn.) at 2.0 µg/ml in 50 mM carbonate coating buffer, pH 9.4 (Thermo Scientific). The next day, the plates were washed with ELISA Wash Buffer ("EWB") (PBS, 0.1% Tween 20) and blocked with 300 µl/well of SuperBlock Blocking Buffer in TBS (Thermo Scientific) for 1 hour at room temperature. The plates were washed with EWB and incubated with 100 µl/well of C-terminal histidine-tagged recombinant human FcγRIIIA/CD16A (F158) (R&D Systems) at 1.3 µg/ml in ELISA Buffer ("EB") (PBS, 1% bovine serum albumin, 0.1% Tween 20) for 2 hours at room temperature. Purified Hu1D10 antibody was serially diluted fourfold starting at 50 µg/ml in EB. The plates were washed with EWB, incubated with 100 µl/well of diluted Hu1D10 antibody for 1 hour at room temperature, and then washed with EWB. 100 µl/well of goat anti-human IgG (H+L) HRP-conjugated antibody (Jackson ImmunoResearch Laboratories) at 1:1000 in EB was then added. After incubation for 1 hour at room temperature, the plates were washed with EWB, followed by addition of 100 µl/well of TMB Substrate (BioFX Laboratories). The reaction was stopped with 100 µl/well of 650 nm Stop Reagent (BioFX Laboratories) and the absorbance at 650 nm was measured using a VERSAmax ELISA Microplate Reader (Molecular Devices).

Results:

The results of a typical experiment are shown in FIG. 6A. Consistent with the literature (Lazar et al., 2006, Proc. Natl. Acad. Sci. 103:4005-4010), the Hu1D10-IgG1 double mutant S239D/I332E had significantly increased FcγRIIIA binding activity compared to the wild-type antibody. Other Hu1D10-IgG1 antibodies containing known mutations—including the K326M/E333S double mutant (Idusogie et al., 2001, J. Immunol. 166:2571-2575), the N276K/A339T double mutant (U.S. Pat. No. 7,994,290), and the H268F/ S324T double mutant (Moore et al., 2010, mAbs 2:181-189)—all had FcγRIIIA binding activity comparable to the wild-type antibody, while the S267E/H268F/S324T triple mutant (Moore et al., 2010, mAbs 2:181-189) had significantly reduced FcγRIIIA binding activity compared to the wild-type antibody. The Hu1D10-IgG1 double mutants S324N/I332F, S324W/I332F, S324N/I332M, S324W/I332M, S324N/I332Y and S324W/I332Y all had modestly reduced FcγRIIIA binding activity compared to the wild-type antibody.

Example 6

Characterization of ADCC Activity of Wild-Type and Mutant Human IgG1 Antibodies

Cell Culture:

Human Burkitt's lymphoma cell line Raji (American Type Culture Collection, Manassas, Va.) was maintained in RPMI 1640 medium (HyClone) containing 10% heat-inactivated FBS (Gibco).

ADCC Assay:

The antibody-dependent cell-mediated cytotoxicity (ADCC) activity of Hu1D10 wild-type and mutant antibodies was measured by Cr-51 release using human peripheral blood mononuclear cells (PBMC) as effectors and Raji cells as targets following a published method (Hinton et al., 2006, J. Immunol. 176:346-356). Target cells were labeled with 50 μCi of Cr-51 (Perkin Elmer, Waltham, Mass.) per 1×10$^6$ cells for 1 hour at 37° C., and resuspended at a density of 0.4×10$^6$ cells/ml in ADCC assay medium ("ADCC-AM") (RPMI 1640, 10% heat-inactivated FBS). PBMC were prepared from fresh whole blood using a Ficoll-Paque Plus gradient (GE Healthcare Biosciences, Pittsburgh, Pa.) and resuspended at a density of 8×10$^6$ cells/ml in ADCC-AM. Hu1D10 wild-type and mutant antibodies were serially diluted in ADCC-AM beginning at 4 μg/ml. Target cells (50 μl/well) and serially diluted Hu1D10 antibody (50 μl/well) were combined in the wells of a Costar TC-treated V-bottom plate (Corning, Corning, N.Y.) and incubated for 30 minutes at 4° C. PBMC (100 μl/well; i.e., 40:1 effector/target ratio) were added to the opsonized cells and incubated for 4 hours at 37° C. in a $CO_2$ incubator. Antibody independent cell-mediated cytotoxicity ("AICC") was measured by incubating effector and target cells in the absence of antibody. Maximum release ("MR") was measured by adding 2% Triton X-100 to target cells. Spontaneous release ("SR") was measured by incubating target cells in the absence of antibody. After 4 hours, the plates were gently centrifuged and Cr-51 release was measured by counting 100 μl of cell-free supernatant in a Wizard 1470 gamma counter (Perkin Elmer). The percent cytotoxicity was calculated using the formula [(Sample−SR)/(MR−SR)]×100.

Results:

The ADCC activity of Hu1D10 wild-type and various mutant antibodies was determined by measuring Cr-51 release from Raji target cells using human PBMC as effector cells. The results of an exemplary experiment are shown in FIG. 6B. Consistent with the literature (Lazar et al., 2006, Proc. Natl. Acad. Sci. 103:4005-4010), the Hu1D10-IgG1 double mutant S239D/I332E had significantly increased ADCC activity compared to the wild-type antibody, while the D265A/N297A double mutant (Wilson et al., 2011, Cancer Cell 19:101-113) had no ADCC activity, as expected. Other Hu1D10-IgG1 antibodies containing described mutations—including the K326M/E333S double mutant (Idusogie et al., 2001, J. Immunol. 166:2571-2575), the N276K/A339T double mutant (U.S. Pat. No. 7,994,290), and the H268F/S324T double mutant (Moore et al., 2010, mAbs 2:181-189)—all displayed ADCC activity comparable to the wild-type antibody. The S267E/H268F/S324T triple mutant (Moore et al., 2010, mAbs 2:181-18) had significantly reduced ADCC activity compared to the wild-type antibody. The Hu1D10-IgG1 double mutants S324N/I332F, S324W/I332F, S324N/I332M, S324W/I332M, S324N/I332Y and S324W/I332Y all showed modestly reduced ADCC activity compared to the wild-type antibody. Thus, the double substitutions at positions 324/332 significantly increase CDC activity without significant deleterious effects on ADCC activity.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A polypeptide comprising a variant Fc domain, which comprises SEQ ID NO:16.

2. The polypeptide of claim 1, which is an antibody.

3. The polypeptide of claim 2, which is a human or humanized antibody.

4. The polypeptide of claim 2, wherein the antibody specifically binds to a costimulatory molecule, a cytokine, a chemokine, an adhesion molecule, an activation markers, or an immunomodulatory protein.

5. The polypeptide of claim 1, which is a bispecific antibody.

6. The polypeptide of claim 1 which is an Fc fusion protein in which the variant Fc domain is operably linked to at least one fusion partner.

7. A pharmaceutical composition comprising the polypeptide of claim 1 and a pharmaceutically acceptable carrier.

8. A polypeptide comprising a variant Fc domain, which comprises SEQ ID NO:15.

9. The polypeptide of claim 8, which is an antibody.

10. The polypeptide of claim 9, which is a human or humanized antibody.

11. The polypeptide of claim 9, wherein the antibody specifically binds to a costimulatory molecule, a cytokine, a chemokine, an adhesion molecule, an activation markers, or an immunomodulatory protein.

12. The polypeptide of claim 8, which is a bispecific antibody.

13. The polypeptide of claim 8 which is an Fc fusion protein in which the Fc domain is operably linked to at least one fusion partner.

14. A pharmaceutical composition comprising the polypeptide of claim 8 and a pharmaceutically acceptable carrier.

* * * * *